(12) United States Patent
Finkel et al.

(10) Patent No.: US 9,326,725 B2
(45) Date of Patent: May 3, 2016

(54) APPARATUS AND METHOD FOR HUMAN ALGOMETRY

(75) Inventors: Julia C. Finkel, Washington, DC (US); Zenaide M. N. Quezado, Washington, DC (US)

(73) Assignee: Children's National Medical Center, Washington, DC (US)

(*) Notice: Subject to any disclaimer, the term of this patent is extended or adjusted under 35 U.S.C. 154(b) by 261 days.

(21) Appl. No.: 13/076,239

(22) Filed: Mar. 30, 2011

(65) Prior Publication Data

US 2011/0245708 A1 Oct. 6, 2011

Related U.S. Application Data

(60) Provisional application No. 61/282,610, filed on Mar. 30, 2010.

(51) Int. Cl.
*A61B 5/04* (2006.01)
*A61B 5/00* (2006.01)
(Continued)

(52) U.S. Cl.
CPC .............. *A61B 5/4824* (2013.01); *A61B 5/0484* (2013.01); *A61B 5/4827* (2013.01); *A61B 5/4839* (2013.01); *A61N 1/36071* (2013.01); *A61B 5/6826* (2013.01)

(58) Field of Classification Search
CPC ...... A61B 5/4824; A61B 5/4848; A61B 5/72; A61B 5/04; A61B 5/04001; A61B 5/0484; A61B 5/4058; A61B 5/0476; A61B 5/048
USPC .................................................. 600/544–545
See application file for complete search history.

(56) References Cited

U.S. PATENT DOCUMENTS

| 4,305,402 A | 12/1981 | Katims |
| 4,503,863 A | 3/1985 | Katims |

(Continued)

FOREIGN PATENT DOCUMENTS

| JP | 2003-149137 | 5/2003 |
| JP | 2003-528679 | 9/2003 |

(Continued)

OTHER PUBLICATIONS

'A Quantitative Analysis of Sensory Function in Lumbar Radiculopathy Using Current Perception Threshold Testing', Yamashita, Toshihiko; Kanaya, Kunihito; Sekine, Masatoshi; Takebayashi, Tsuneo; Kawaguchi, Satoshi; Katahira, Genichirou; Spine: Jul. 15, 2002—vol. 27—Issue 14—pp. 1567-1570.*

(Continued)

*Primary Examiner* — Etsub Berhanu
*Assistant Examiner* — Karen Toth
(74) *Attorney, Agent, or Firm* — Oblon, McClelland, Maier & Neustadt, L.L.P.

(57) ABSTRACT

An apparatus and method for performing human algometry are disclosed. They include a stimulator configured to apply electrical stimulation of variable intensity to an area of a patient's body, a monitoring device configured to measure a level of cortical activity in one or more regions of the patient's brain, and a microprocessor connected to the stimulator and the monitoring device that is configured to correlate the intensity of the electrical stimulation with the level of activity in the one or more regions of the patient's brain and to determine at least one of a measurement of pain intensity, a measurement of a sensory detection threshold (SDT), a measurement of a drug's analgesic impact, an indication of an onset of tolerance to a drug, an indication of an onset of analgesic-induced hyperalgesia, an indication of conditions of allodynia, a measurement of dose-response characteristics of pain management drugs, and a characterization of a pain condition.

7 Claims, 21 Drawing Sheets

(51) Int. Cl.
*A61B 5/0484* (2006.01)
*A61N 1/36* (2006.01)

(56) References Cited

U.S. PATENT DOCUMENTS

| | | | |
|---|---|---|---|
| 4,570,638 A | | 2/1986 | Stoddart et al. |
| 4,725,147 A | | 2/1988 | Stoddart |
| 4,768,516 A | | 9/1988 | Stoddart et al. |
| 4,817,623 A | | 4/1989 | Stoddart et al. |
| 4,869,264 A | * | 9/1989 | Silberstein ............ 600/544 |
| 5,139,025 A | | 8/1992 | Lewis et al. |
| 5,140,989 A | | 8/1992 | Lewis et al. |
| 5,217,013 A | | 6/1993 | Lewis et al. |
| 5,335,657 A | | 8/1994 | Terry, Jr. et al. |
| 5,349,961 A | | 9/1994 | Stoddart et al. |
| 5,465,714 A | | 11/1995 | Scheuing |
| 5,477,853 A | | 12/1995 | Farkas et al. |
| 5,482,034 A | | 1/1996 | Lewis et al. |
| 5,584,296 A | | 12/1996 | Cui et al. |
| 5,697,367 A | | 12/1997 | Lewis et al. |
| 5,795,292 A | | 8/1998 | Lewis et al. |
| 5,797,854 A | | 8/1998 | Hedgecock |
| 5,806,522 A | | 9/1998 | Katims |
| 5,902,235 A | | 5/1999 | Lewis et al. |
| 6,381,480 B1 | | 4/2002 | Stoddart et al. |
| 6,397,099 B1 | | 5/2002 | Chance |
| 6,526,297 B1 | | 2/2003 | Merilainen |
| 6,615,065 B1 | | 9/2003 | Barrett et al. |
| 6,654,632 B2 | | 11/2003 | Lange et al. |
| 6,751,499 B2 | | 6/2004 | Lange et al. |
| 6,757,558 B2 | | 6/2004 | Lange et al. |
| 6,826,426 B2 | | 11/2004 | Lange et al. |
| 6,830,711 B2 | | 12/2004 | Mills et al. |
| 7,326,181 B2 | | 2/2008 | Katims |
| 7,392,074 B2 | | 6/2008 | Isaacson et al. |
| 7,634,315 B2 | | 12/2009 | Cholette |
| D613,413 S | | 4/2010 | Gonopolskiy et al. |
| D615,657 S | | 5/2010 | Anderson et al. |
| D615,658 S | | 5/2010 | Anderson et al. |
| D615,659 S | | 5/2010 | Anderson et al. |
| D615,660 S | | 5/2010 | Anderson et al. |
| 7,741,592 B1 | | 6/2010 | Gonopolskiy et al. |
| 7,844,324 B2 | | 11/2010 | Sarkela et al. |
| 7,865,223 B1 | | 1/2011 | Bernreuter |
| 2002/0042563 A1 | | 4/2002 | Becerra et al. |
| 2002/0173723 A1 | | 11/2002 | Lewis et al. |
| 2003/0181791 A1 | * | 9/2003 | Thomas et al. ............ 600/300 |
| 2003/0204148 A1 | | 10/2003 | Lange et al. |
| 2003/0236469 A1 | | 12/2003 | Hedgecock |
| 2004/0039267 A1 | | 2/2004 | Kawasaki et al. |
| 2004/0082862 A1 | | 4/2004 | Chance |
| 2005/0020905 A1 | | 1/2005 | Siddall et al. |
| 2005/0272984 A1 | | 12/2005 | Huiku |
| 2006/0004296 A1 | | 1/2006 | Huiku et al. |
| 2006/0052720 A1 | | 3/2006 | Ross et al. |
| 2006/0089551 A1 | * | 4/2006 | England ............ A61B 5/055 600/411 |
| 2007/0055118 A1 | | 3/2007 | Kawasaki et al. |
| 2008/0208784 A1 | * | 8/2008 | Hill et al. ............ 706/46 |
| 2008/0249430 A1 | * | 10/2008 | John et al. ............ 600/544 |
| 2008/0269847 A1 | | 10/2008 | Nemenov |
| 2008/0306365 A1 | | 12/2008 | Bunce et al. |
| 2009/0076372 A1 | | 3/2009 | England |
| 2009/0163775 A1 | | 6/2009 | Barrett et al. |
| 2009/0220425 A1 | | 9/2009 | Moxon et al. |
| 2009/0259114 A1 | | 10/2009 | Johnson et al. |
| 2009/0309645 A1 | | 12/2009 | Isaacson et al. |
| 2010/0130840 A1 | | 5/2010 | Isaacson |
| 2010/0152543 A1 | | 6/2010 | Heneghan et al. |
| 2010/0210924 A1 | | 8/2010 | Parthasarathy et al. |
| 2011/0087125 A1 | * | 4/2011 | Causevic ............ 600/544 |
| 2011/0118661 A1 | * | 5/2011 | Pless et al. ............ 604/66 |
| 2011/0245709 A1 | * | 10/2011 | Greenwald ............ 600/544 |
| 2012/0221075 A1 | * | 8/2012 | Bentwich ............ 607/45 |
| 2012/0296569 A1 | * | 11/2012 | Shahaf et al. ............ 702/19 |
| 2012/0316622 A1 | * | 12/2012 | Whitehurst et al. ............ 607/62 |

FOREIGN PATENT DOCUMENTS

| | | |
|---|---|---|
| JP | 2007-130034 | 5/2007 |
| JP | 2009-532130 | 9/2009 |
| WO | 2006071891 A2 | 7/2006 |
| WO | WO 2006/071891 A2 | 7/2006 |
| WO | WO 2008/124566 A2 | 10/2008 |

OTHER PUBLICATIONS

American Medical Association, "Module 6: Pediatric Pain Management", Pain Management Series, http://www.ama-cmeonline.com/pain_mgmt/module06/ index.htm (Feb. 2010).

Angst et al., "Pharmacodynamics of orally administered sustained-release hydromorphone in humans", Anesthesiology, 2001, vol. 94, No. 1, pp. 63-73.

Bartocci et al., "Pain activates cortical areas in the preterm newborn brain", Pain, 2006, vol. 122, No. 1-2, pp. 109-117.

Becerra et al., "Diffuse Optical Tomography Activation in the Somatosensory Cortex: Specific Activation by Painful vs. Non-Painful Thermal Stimuli", PLoS One, 2009, vol. 4, No. 11, pp. 1-5.

Becerra et al., "Diffuse Optical Tomography of Pain and Tactile Stimulation: Activation in Cortical Sensory and Emotional Systems", Neuroimage, 2008, vol. 41, No. 2, pp. 252-259.

Bornhovd et al., "Painful stimuli evoke different stimulus-response functions in the amygdala, prefrontal, insula and somatosensory cortex: a single-trial fMRI study", Brain, 2002, vol. 125, No. 6, pp. 1326-1336.

Brennum et al., "Quantitative sensory examination of epidural anaesthesia and analgesia in man: effects of pre- and post-traumatic morphine on hyperalgesia", Pain, 1994, vol. 59, No. 2, pp. 261-271.

Carbajal et al., "Epidemiology and Treatment of Painful Procedures in Neonates in Intensive Care Units", JAMA, 2008, vol. 300. No. 1, pp. 60-67.

De Pascalis et al., "Pain perception, obstructive imagery and phase-ordered gamma oscillations", International Journal of Psychophysiology, 2005, vol. 56 No. 2, pp. 157-169.

Finkel et al., "Effects of aging on current vocalization threshold in mice measured by a novel nociception assay", Anesthesiology, 2006, vol. 105, No. 2, pp. 360-369.

Finkel et al., "Neuro-selective sensory electrodiagnostic evaluation of 4% liposomal topical lidocaine", Anesthesiology Analgesic, 2002, vol. 94, No. 5, pp. 1259-1262, Table of Contents.

Gustorff et al., "Comparison of different quantitative sensory testing methods during remifentanil infusion in volunteers", British Journal of Anaesthesiology, 2003, vol. 91 No. 2, pp. 203-208.

Hoshi et al., "Dynamic multichannel near-infrared optical imaging of human brain activity", American Physiological Society, 1993, pp. 1842-1846.

Kalinowski et al., "Sedation and pain management in interventional radiology", Adjunctive Therapy, pp. 14-18.

Katims, J. J., "Electrodiagnostic Functional Sensory Evaluation of the Patient with Pain: A Review of the Neuroselective Current Perception Threshiold and Pain Tolerance Threshold", Pain Digest, 1998, vol. 8, pp. 219-230.

Katims, J. J., "Neuro-selective current perception threshold quantitative sensory test", Muscle Nerve, 1997, vol. 20 No. 11, pp. 1468-1469.

Katims et al., "Transcutaneous nerve stimulation: Frequency and waveform specificity in humans", Applied Neurophysiology, 1986, vol. 49, No. 1-2, pp. 86-91.

Kiso et al., "Neurometer measurement of current stimulus threshold in rats", Journal of Pharmacological Experimental Therapy, 2001, vol. 297, No. 1, pp. 352-356.

Koga et al., "Selective activation of primary afferent fibers evaluated by sine-wave electrical stimulation", Molecular Pain, 2005, vol. 1, No. 1, Issue 13.

(56) References Cited

OTHER PUBLICATIONS

Liu et al., "Quantitative assessment of differential sensory nerve block after lidocaine spinal anesthesia", Anesthesiology, 1995, vol. 82 No. 1, pp. 60-63.

Liu et al., "The effects of electrical stimulation at different frequencies on perception and pain in human volunteers: epidural versus intravenous administration of fentanyl", Anesthesiology Analgesic, 1996, vol. 82, No. 1, pp. 98-102.

Lotsch et al., "The Mu-opioid agonist remifentanil attenuates hyperalgesia evoked by blunt and punctuated stimuli with different potency: a pharmacological evaluation of the freeze lesion in humans", Pain, 2003, vol. 102, No. 1-2, pp. 151-161.

Luginbuhl et al., "Comparison of five experimental pain tests to measure analgesic effects of alfentanil", Anesthesiology, 2001, vol. 95, No. 1, pp. 22-29.

Macleon, David B., "Calibration and Validation of the Nonin Non-invasive Regional Oximeter with Cerebral Sensor", Press Release (www.nonin.com).

Maltseva et al., "Alpha oscillations as an indicator of dynamic memory operations—anticipation of omitted stimuli", International Journal of Psychophysiology, 2000, vol. 36, No. 3, pp. 185-197.

McGowan et al., "Synergy of a Combined Near-Infrared Spectroscopy and Blood Oxygenation Level-Dependent Functional Activation Study," American Journal of Neuroradiology, Aug. 25, 2004, pp. 1127-1128.

Oda et al., "Quantitative and fiber-selective evaluation of dose-dependent nerve blockade by intrathecal lidocaine in rats", Journal of Pharmacological Experimental Therapy, 2005, vol. 312, No. 3, pp. 1132-1137.

Owen-Reece et al., "Near infrared spectroscopy", British Journal of Anaesthesiology, 1999, vol. 82, No. 3, pp. 418-426.

Pedersen et al., "Secondary hyperalgesia to heat stimuli after burn injury in man," Pain, 1998, vol. 76. No. 3, pp. 377-384.

Posner et al., "Effects of an opiate on cold-induced pain and the CNS in healthy volunteers," Pain, 1985, vol. 23, No. 1, pp. 73-82.

Slater et al., "Cortical pain responses in the infant brain," Pain, 2006, vol. 123 No. 3, pp. 332-334.

Slater et al., "Cortical pain responses in human infants," Journal of Neuroscience, 2006, vol. 26, No. 14, pp. 3662-3666.

Slater et al., "Can cortical responses following noxious stimulation inform us about pain processing in neonates?," Seminars in Perinatology, 2007, vol. 31, No. 5, pp. 298-302.

Tai et al., "Single-trial classification of NIRS signals during emotional induction tasks: towards a corporeal machine interface", Journal of NeuroEngineering and Rehabilitation, 2009, col. 6, vol. 39, pp. 1-14.

Tay et al., "Quantitative assessment of differential sensory blockade after lumbar epidural lidocaine," Anesthesiology Analgesic, 1997, vol. 84, No. 5, pp. 1071-1075.

Tobias, J. D., "Cerebral oxygenation montoring: near-infrared spectroscopy," Future Drugs, 2006, pp. 235-243.

Wolf, et al., "Advances in Near-Infrared Spectroscopy to Study the Brain of the Preterm and Term Neonate", Clinical Perinatology, 2009, col. 36, pp. 807-834.

Wray, et al., "Characterization of the near infrared absorption spectra of cytochrome aa3 and haemoglobin for the non-invasive monitoring of cerebral oxygenation," Biochimica Biophysica Acta, 1988, vol. 933, No. 1, pp. 184-192.

Yarnitsky et al., "Multiple session experimental pain measurement," Pain, 1996, vol. 67, No. 2-3, pp. 327-333.

The Extended European Search Report issued Jul. 18, 2013, in Application No. / U.S. Pat. No. 11766503.4-1657 / 2552302 PCT/US2011030546.

Communication pursuant to Rules 70(2) and 70a(2) EPC issued Aug. 6, 2013, in Application No. / U.S. Pat. No. 11766503.4-1657 / 2552302 PCT/US2011030546.

Japanese Office Action issued Jul. 28, 2015 in Patent Application No. 2013-502806 (with English Translation).

Japanese Office Action issued Nov. 4, 2014, in Japan Patent Application No. 2013-502806 (with English translation).

\* cited by examiner

PIPP SCALE

| Pain Score | Degree of Pain | Observation |
|---|---|---|
| 0 | No Apparent Pain | - Not Crying, Resting, Calm, Sleeping<br>- Relaxed Body Posture<br>- Comfortable Without Intervention<br>- Within Baseline HR, B/P, Respiratory |
| 1 | Uncomfortable | - Intermittent Whimpering, Cry, Restlessness, But Able to Sleep<br>- Intermittently Tense Muscles<br>- Comforts, Calms Self<br>- Increase in HR by 5-10 BPM |
| 2 | Mild Pain | - Whimpering Cry, Moaning, Restless, Irritable, But Able to Sleep<br>- Tense Muscles<br>- Difficult to Distract and Console,<br>- Increase in HR by 10-15 BPM, Periodic Breathing |
| 3 | Moderate Pain | - Sobbing, Strong, Loud Cry, Continuous Restlessness, Irritability, Sleep Disruption<br>- Tense, Rigid Body<br>- Only Intermittently Distractible<br>- Increase in HR by 15-25 BPM, Increase in BP by 10mm Hg |
| 4 | Sever Pain | - High Pitched Scream<br>- Thrashing, Tremulous<br>- Unable to Sleep, Very Still<br>- Increase in HR by >25 BPM, Apnea or Tachypnea |

**FIGURE 1E
(PRIOR ART)**

CRIES SCALE

| Observations | 0 | 1 | 2 | Score |
|---|---|---|---|---|
| Breathing Independent of Vocalization | Normal | - Occasional labored breathing.<br>- Short period of hyperventilation. | - Noisy labored breathing.<br>- Long period of hyperventilation.<br>- Cheyne-Stokes respirations. | |
| Negative Vocalization | None | - Occasional moan or groan.<br>- Low-level speech with a negative or disapproving quality. | - Repeated troubled calling out.<br>- Loud moaning or groaning.<br>- Crying. | |
| Facial Expression | Smiling or Inexpressive | - Sad.<br>- Frightened.<br>- Frown. | - Facial grimacing. | |
| Body Language | Relaxed | - Tense.<br>- Distressed pacing.<br>- Fidgeting. | - Rigid.<br>- Fists clenched.<br>- Knees pulled up.<br>- Pulling or pushing away.<br>- Striking out. | |
| Consolability | No Need to Console | - Distracted or reassured by voice or touch. | - Unable to console, distract or reassure. | |
| | | | TOTAL: | |

**FIGURE 1F
(PRIOR ART)**

FIFGURE 15

APPARATUS AND METHOD FOR HUMAN ALGOMETRY

CROSS-REFERENCE TO RELATED APPLICATIONS

The present application claims the benefit of U.S. Provisional Application No. 61/282,610, filed Mar. 30, 2010, the entire contents of which are hereby incorporated by reference as if fully set forth herein.

FIELD OF THE INVENTION

The present invention relates to a pain assessment apparatus and method that allows for the objective measurement of pain for use in quantitatively grading pain intensity and sensory detection thresholds (SDTs), determining responses to analgesics, assessing the efficacy and dose-response relationships of newly developed and/or investigational drugs targeted for the management of pain, providing an objective characterization of pain conditions, identifying the onset of tolerance and/or analgesic-induced toxicity from different drugs and pain interventions, and guiding pain management. More particularly, the present invention relates to a pain assessment apparatus and method that uses neuro-selective electrical stimulation in combination with cortical activity monitoring to provide an objective, qualitative, and quantitative measure of pain based on hemodynamic and/or neurophysiological responses to sub-noxious, neuro-specific electrical stimulation and/or manually applied noxious stimulation.

BACKGROUND OF THE INVENTION

Healthcare providers are frequently faced with the problem of diagnosing and treating patients suffering from varying levels of pain. The appropriate assessment of a patient's pain is a prerequisite to successful diagnosis and treatment of the pain. However, healthcare providers often have difficulty in making such assessments due to patients' inability to accurately describe the pain that they are experiencing. Those difficulties sometimes result in ineffective, inadequate, and/or excessive treatments.

In more detail, the experience of pain has at least two components: 1) a "sensory", or nociceptive, component, and 2) an "affective", or emotional, component. The sensory component comprises the sensory modality of nociception experienced within the somatosensory system in response to certain stimuli, such as nerve fibers carrying information regarding the stimuli to the patient's brain. The affective component comprises feelings of unpleasantness and other emotions associated with the future implications related to pain, such as annoyance, fear, or distress.

Traditionally, healthcare providers have used varying apparatus/methods for subjectively, qualitatively, and/or semi-quantitatively measuring the amount and/or intensity of pain that a patient is suffering. The predominant apparatus/methods that have been used are categorical pain descriptors. For example, FIG. 1A illustrates a verbal pain intensity scale that is used to measure pain intensity based on adjective descriptors (e.g., "no pain", "mild pain", "moderate pain", "severe pain", "very severe pain", and "worst pain possible"); FIG. 1B illustrates a numerical pain intensity scale that is used to measure pain intensity based on a numerical rating (i.e., 0 for "no pain" up to 10 for "worst pain possible"); FIG. 1C illustrates a visual analog scale (VAS) that is used to measure pain intensity based on a position along a continuous line between two endpoints (i.e., the closer to the left end point the closer to "no pain" and the closer to the right end point the closer to "worst pain possible"); FIG. 1D illustrates a Wong-Baker pain intensity scale that is used to measure pain intensity based on a face that best represents how the patient is feeling (e.g., a face with the largest smile for "no hurt" and a face that is crying for "hurts worst"); FIG. 1E illustrates a premature infant pain profile (PIPP) pain assessment scale that is used to measure pain based on a score that corresponds to a specific behavioral observation (i.e., a "relaxed body posture" corresponds to "no apparent pain" and "thrashing" corresponds to "severe pain"); and FIG. 1F illustrates a crying, requires oxygen, increased vital signs, expression, and sleepless (CRIES) pain assessment scale that is used to measure pain based on a score that is totaled from a plurality of different behavioral observations (i.e., a "normal" breathing corresponds to a score of 0 and "facial grimacing" corresponds to a score of 2). As those figures illustrate, categorical pain descriptors can be verbal, numerical, visual, observational, or a combination thereof.

The verbal pain intensity scale of FIG. 1A, the numerical pain intensity scale of FIG. 1B, and the VAS of FIG. 1C are generally used in assessing pain intensity in cognitive adults. Those apparatus/methods require a patient to comprehend a physician's or practitioner's questions regarding their pain and to be able to convey, verbally or by otherwise indicating, where they believe their pain falls on each scale to allow for some diagnostic evaluation. The healthcare provider asks the patient to describe his or her pain using corresponding categorical descriptors and then marks the appropriate portion of the scale according to the response.

Those methods cannot be used in patients who cannot convey the intensity or location of their pain to a physician or practitioner (e.g., patient's unable to comprehend their pain or a physician's queries, "non-verbal" patients or otherwise verbally or cognitively challenged patients, patients with developmental disabilities, etc.). Accordingly, the Wong-Baker pain intensity scale of FIG. 1D is used to measure pain intensity in children and cognitively impaired adults. And the PIPP pain assessment scale of FIG. 1E and the CRIES pain assessment scale of FIG. 1F are generally used to measure pain intensity in infants and non-verbal patients. Those two apparatus/methods rely solely on the healthcare provider's observations.

Other apparatus/methods for pain assessment suffer from similar shortcomings. For example, pain tolerance threshold (PTT) and pain perception threshold (PPT) determinations both rely of verbal response from a patient. Those determinations are subjective and semi-quantitative and use electrical stimulation to directly excite both large and small diameter sensory nerve fibers. The PPT determination represents the minimum amount of a potentially noxious electrical stimulus that can be perceived, while the PTT determination represents the maximum amount of noxious electrical stimulus that can be tolerated when used as a clinical diagnostic tool. Thus, PTT determinations are not only dependent on a patient's subjective verbal responses, they also require the patient to experience some amount of aversive stimulus, which not only causes the patient undesirable discomfort, it also elicits the emotional component of pain.

Similarly, the apparatus/methods available for diagnosing neuropathic pain require patient self reporting on the intensity of his or her pain and of its characteristics (e.g., burning, lancinating, throbbing, etc.). That requirement demands a certain level of sophistication and cognitive abilities that is lacking in patients with developmental delay, who are non-verbal, or who are very young. Moreover, it requires the patient's subjective input to execute the testing paradigm.

By virtue of the categorical limitations inherent in the conventional apparatus/methods illustrated discussed above, a healthcare provider inevitably encounters varying descriptions of the same levels of pain intensity from patient to patient, particularly in view of the highly subjective nature of the emotional component of pain. Different people can have different pain thresholds, and those pain thresholds can vary based on outside influences, such as distractions and mood. Those contextual and cognitive factors are partly the result of the fact that pain most often occurs as part of a traumatic event, such as injury or disease. For example, a patient's nociceptive pain in response to noxious stimulation may be accompanied by feelings of annoyance, fear, distress, and/or suffering. Accordingly, patients experiencing the same level of nociceptive pain may describe that pain differently, resulting in different diagnoses and treatments. Those problems are exacerkated when the patient cannot provide a description of their pain and the healthcare provider must rely solely on his or her own physical observations of the patient, such as with young children, infants, neonates, non-verbal patients, and patients with developmental disabilities.

The nociceptive component of pain may also be subjective to specific patients. For example, a patient may experience an exaggerated reaction to nociceptive pain if he or she is suffering from hyperalgesia. A patient may experience an increased sensitivity to nociceptive pain as part of sickness behavior (i.e., the evolved response to illness). And a patient may experience nociceptive pain from stimulus that does not normally provoke such pain if he or she is suffering from allodynia. Accordingly, some patients may be more sensitive to pain than others and, therefore, may experience nociceptive pain out of proportion to physical findings, making it particularly difficult to properly diagnose and treat those patients.

In addition to the different subjective components of pain experienced by a patient, a patient may also inadvertently attempt to sabotage the assessment of his or her pain. For example, the patient may be unwilling to communicate the extent of his pain or fear that he or she will be seen by the healthcare provider as a bother or drug seeker. Or the patient's attitude toward his or her ailment may be depressed and fatalistic, causing him or her to feel that the pain is inevitable and must be tolerated. Some healthcare providers may even adopt an attitude that pain is inevitable and must be tolerated or allow personal prejudice or bias to interfere with the independence of their assessment. Thus, there are many subjective factors—both internal and external to a patient—that can potentially bias pain assessment, thereby resulting in inaccurate diagnoses and ineffective, inadequate, and/or excessive treatments.

Those subjective factors not only negatively affect the diagnosis and treatment of pain, they also negatively affect clinical trials on the efficacy of drugs used in the management of pain (i.e., analgesics and other pain interventions). The main outcome variables in such clinical trials are pain relief and pain reduction. But because of the highly interindividual variability of the results obtained with conventional pain assessment apparatus/methods, it is difficult to obtain an objective measure of pain relief and pain reduction (i.e., efficacy) in clinical trials or other clinical evaluations. Thus, the results of those clinical trials are limited in their accuracy and, therefore, usefulness.

Not only is it difficult to objectively measure the efficacy of analgesics with conventional pain assessment apparatus/methods, long-term and/or high dose use of certain analgesics may exacerbate that difficulty. For example, long-term and/or high-dose use of opioids (e.g. morphine, heroin, hydrocodone, oxycodone, and methadone) may result in a patient developing an increased sensitivity to noxious stimuli (i.e., opioid-induced hyperalgesia) and/or evolving a painful response to previously non-noxious stimuli (i.e., opioid-induced allodynia). However, those forms of opioid-induced toxicity present a similar net effect as tolerance to opioids, making them difficult to distinguish from tolerance in a clinical setting. And while increasing the dose of an opioid can be an effective way to overcome tolerance, doing so to compensate for opioid-induced hyperalgesia or allodynia may paradoxically worsen the patient's condition by increasing sensitivity to pain while escalating physical dependence. In such cases, the patient may actually benefit from complete withdrawal of opioid treatment. Therefore, it is of the utmost importance for healthcare providers to be able to diagnose, quantify, and distinguish actual pain from treatment-induced side effects. In addition, it is of a great deal of importance for healthcare providers to be able to identify the development of such forms of opioid-induced toxicity so they can be distinguished from tolerance and the appropriate therapy can be instituted.

As set forth above, there is a need in the art for an apparatus and method for objectively and quantitatively assessing and characterizing pain in patients—particularly, in young children, infants, neonates, and non-verbal patients or otherwise verbally or cognitively challenged patients, such as patients with developmental disabilities. There is also a need in the art for an apparatus and method for objectively measuring the effect of currently used analgesics and other pain interventions, and to objectively measure the efficacy and dose-response relationships of newly developed and/or investigational drugs and interventions targeted for pain management. And there is a need in the art for an apparatus and method for detecting the onset of tolerance and/or analgesic-induced toxicity to such analgesics. Moreover, multiple lines of evidence suggest that repeated and prolonged pain exposure in neonates, at a time when it is developmentally unexpected, alters their subsequent pain processing, long-term development, and behavior. Therefore, the proper diagnosis, quantification of pain, and appropriate pain therapy during the neonatal period is of utmost importance to prevent such alterations in pain processing pathways after the neonatal period.

SUMMARY OF THE INVENTION

To address at least the problems and/or disadvantages described above, it is a non-limiting object of the present invention to provide an apparatus and method for human algometry. The apparatus and method include a stimulator configured to apply electrical stimulation of variable intensity to an area of a patient's body, a monitoring device configured to measure a level of cortical activity in one or more regions of the patient's brain, and a microprocessor connected to the stimulator and the monitoring device that is configured to correlate the intensity of the electrical stimulation with the level of activity in the one or more regions of the patient's brain and to determine at least one of a measurement of pain intensity, a measurement of a sensory detection threshold (SDT), a measurement of a drug's analgesic impact, an indication of an onset of tolerance to a drug, an indication of an onset of analgesic-induced hyperalgesia, an indication of conditions of allodynia, a measurement of dose-response characteristics of pain management drugs, and a characterization of a pain condition. Those and other objects, advantages, and features of the present invention will become more readily apparent by the following written description, taken in conjunction with the accompanying drawings and claims.

BRIEF DESCRIPTION OF THE DRAWINGS

Aspects of the present invention can be better understood with reference to the following drawings, which are part of the specification and represent preferred embodiments of the present invention. The components in the drawings are not necessarily to scale, emphasis instead being placed upon illustrating the principles of the present invention.

FIGS. 1A-1F are diagrams that illustrate examples of conventional pain assessment apparatus/methods;

DETAILED DESCRIPTION OF THE PREFERRED EMBODIMENTS

Figure 1A:
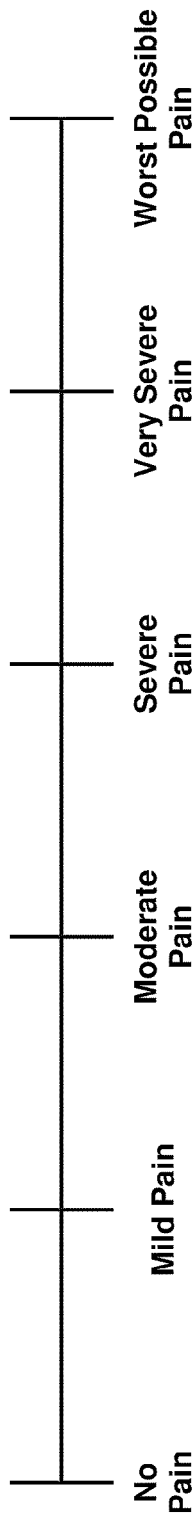
Figure 1B:
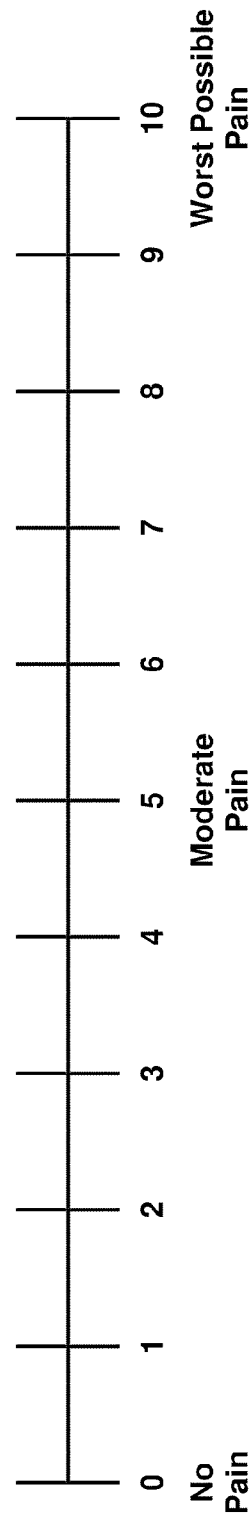
Figure 1C:
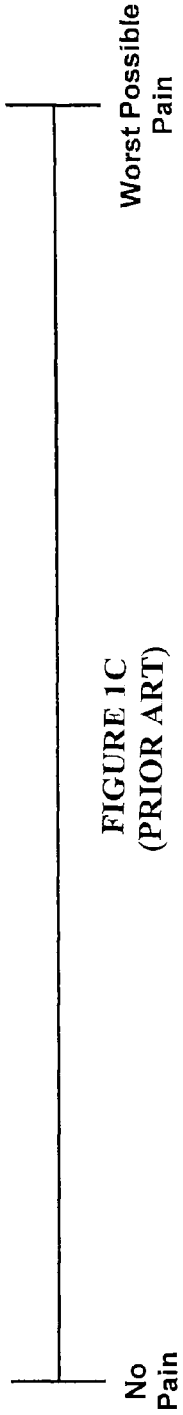
Figure 1D:
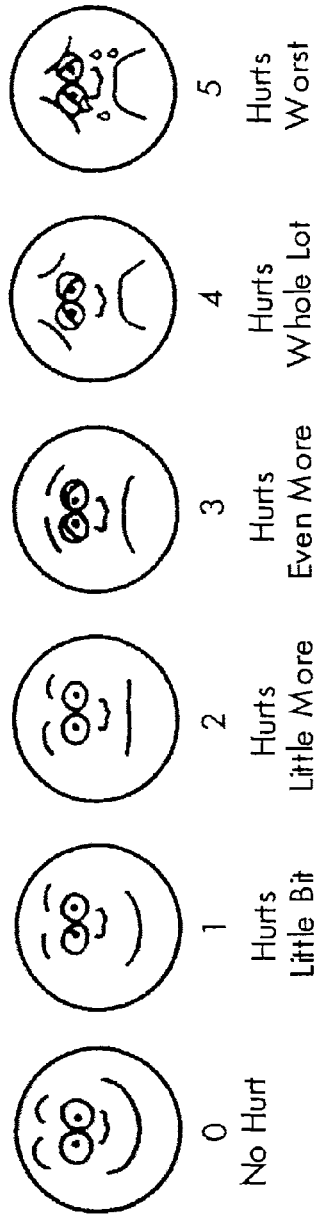

The present invention overcomes the shortcomings of the prior art and provides at least the advantages discussed below by integrating neuro-specific electrical stimulation with cortical activity monitoring to obtain an objective, qualitative, and quantitative measurement of pain, sensory detection thresholds (SDTs), the analgesic effects of drugs and other pain interventions, the pharmacodynamic impact of analgesics and other pain interventions, the efficacy and dose-response relationships of novel investigational drugs and other interventions targeted for the management of pain, and the onset of tolerance and/or analgesic-induced toxicity from different drugs and paint interventions. The present invention also provides for the objective characterization of different pain conditions (e.g., neuropathic pain, hyperalgesia, allodynia, etc.). In more detail, neuro-specific electrical stimulation is applied to a patient incrementally until it causes activation of specific sensory nerve fibers (i.e., until a threshold action potential is generated at the targeted nerve fiber), but without inciting the emotional component of pain. In other words, sensory nerve fibers are activated up to the point where sensation is detected without overt pain and without any bodily harm. And because the patient will not incur overt pain, cortical activity monitoring technology is used to measure the level of nociception experienced by the patient. The present invention integrates those technologies to provide a direct correlation of the measured level of nociception experienced by the patient with the type of neuro-specific electrical stimulation being applied to provide an objective, qualitative, and quantitative measurement of the patient's response to that stimulation.

The patient's measured response to the neuro-specific electrical stimulation is used to determine that patient's SDT and to provide a diagnostic characterization of the patient's stimulus response (e.g., neuropathic pain, hyperalgesia, allodynia, etc.). That measured response is also used to determine the analgesic impact of different drugs and pain interventions on the patient's SDT, depending on the type of neuro-specific electrical stimulation that is applied. And by repeating those measurements over time, the present invention can also detect the onset of tolerance and/or analgesic-induced toxicity from different drugs. Accordingly, the present invention not only provides an apparatus and method for objectively and quantitatively assessing pain in patients, it also provides an apparatus and method for objectively measuring the analgesic effect drugs and other pain interventions, measuring the efficacy and dose-response relationships of novel investigational drugs and other interventions targeted for the management of pain, and objectively characterizing pain conditions.

Those and other advantages provided by the present invention can be better understood from the description of the preferred embodiments below and in the accompanying drawings. In describing the preferred embodiments, specific terminology is resorted to for the sake of clarity. However, the present invention is not intended to be limited to the specific terminology so selected, and it is to be understood that each specific term includes all technical equivalents that operate in a similar manner to accomplish a similar purpose. For example, the terms "Aβ fiber", "Aδ fiber", and "C fiber" are used not only to refer specifically to the primary nerve fibers in human skin, they are also used to refer more generally to the corresponding nerve fibers in muscles, joints, and viscera (e.g., Group II, III, and IV nerve fibers).

A. Neuro-Specific Electrical Stimulation

The somatosensory system comprises receptors and processing centers that produce sensory modalities such as touch, temperature, body position, and pain. Sensory receptors are nerve endings that cover the skin and epithelia, skeletal muscles, bones and joints, and viscera of the human body. Those sensory receptors are innervated by different types of nerve fibers and initiate sensory transduction in response to stimuli by creating graded potentials or action potentials in the same cell or in an adjacent cell. Those nerve fibers can be classified based on such characteristics as axonal conduction velocity, refractory period, fiber size, and mylenation.

Figure 2:
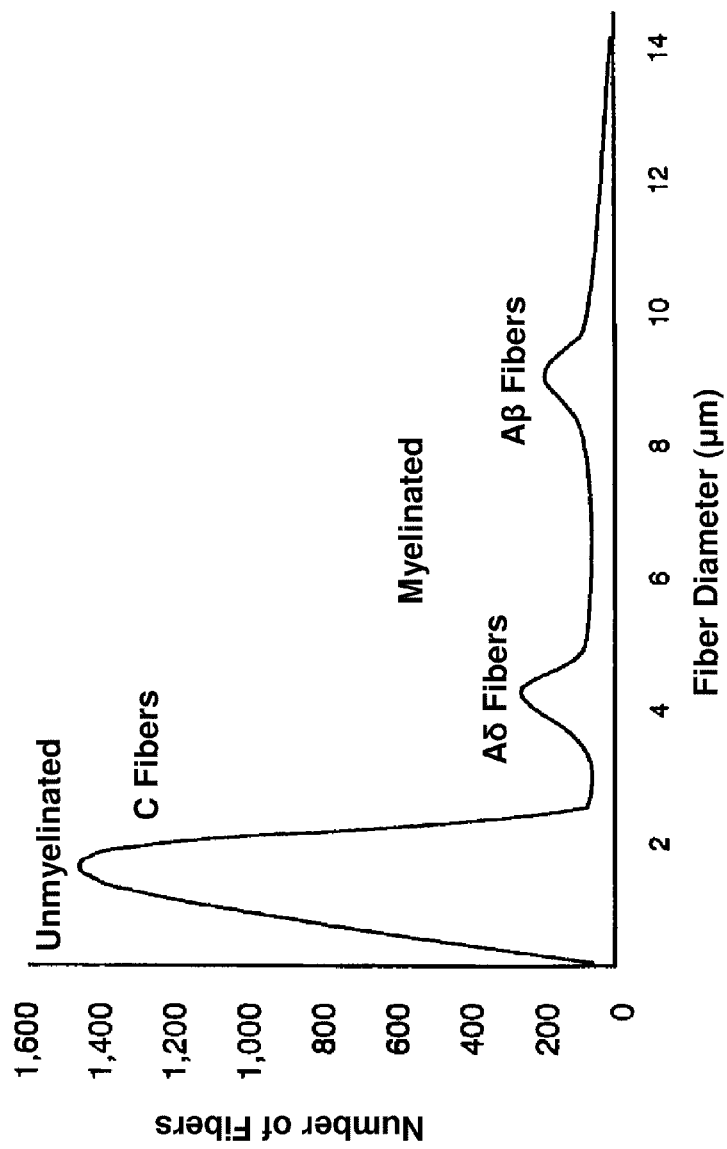
FIG. 2 includes a graph illustrating the nerve-fiber-diameter distribution of a typical human sensory nerve and a chart listing neuro-specific electrical stimulation for those nerve fibers according to a non-limiting embodiment of the present invention.

Turning to the drawings, FIG. 2 includes a graph illustrating the nerve-fiber-diameter distribution of a typical human sensory nerve and a chart listing corresponding nerve fiber characteristics. A typical human sensory nerve comprises primary afferent fibers bundled together. The primary fibers in human skin include large-diameter (e.g., 5-12 μm) myelinated A-beta (Aβ) fibers, medium-diameter (i.e., 2-5 μm) myelinated A-delta (Aδ) fibers, and small-diameter (i.e., 0.2-1.5 μm) unmyelinated C fibers. The primary fibers in human muscles are subdivided into analogous groups of myelinated axons—Group II fibers, which are analogous to Aβ fibers; Group III fibers, which are analogous to Aδ fibers; and Group IV fibers, which are analogous to C fibers. And the primary fibers in joints include Groups II, III, and IV fibers as well as Group I fibers, the latter of which do not have analogous skin fibers but are similar to Act muscle fibers. Each of those major fiber types has its own characteristic neurophysiological profile, sensory function, depolarization characteristics and sensation evoked by electrical stimulation, and conduction block susceptibility.

For example, Aβ fibers are linked with various cutaneous mechanoreceptors and a small number of visceral mechanoreceptors, and Group I and II fibers are linked with muscle mechanoreceptors and joint mechanoreceptors. Aβ and Group I and IT fibers are considered "low threshold" fibers because they detect non-noxious stimuli to the skin (e.g., skin indentation, skin and hair movement, vibration of the skin and hair, etc.), muscles (e.g., changes in muscle length, muscle tension, muscle contraction, vibration of the muscle, etc.), and joints (e.g., distension of the joint, contraction of the joint, vibration of the joint, etc.). Aβ and Group II fibers have a quick conduction velocity (e.g., 30-75 m/s and 24-71 m/s, respectively), with Group I fibers having an even quicker conduction velocity (e.g., 72-120 m/s). Aβ and Group II fibers typically conduct impulses that signal the perception of touch, pressure, and/or vibration. Conduction of such signals is most susceptible to blockage by applying compression to the affected area.

Aδ, C, and Group III and IV fibers are linked with mechanoreceptors, thermoreceptors, and polymodal nociceptors. They are considered "high threshold" fibers because they detect a higher intensity of stimulation (i.e., noxious stimulation) than Aβ and Group I and II fibers (i.e., non-noxious stimulation). They detect noxious stimulation to the skin (e.g., intense pressure, severe temperatures, damage to skin tissue, etc.), muscles (e.g., intense pressure, ischemia, damage to muscle tissue, etc.), and joints (e.g., extreme bending, innocuous movement, probing of the joint, etc.). Some of those fibers do not differentiate noxious from non-noxious stimuli, while others respond only to painfully intense stimuli.

Aδ and Group III fibers have an intermediate conduction velocity (e.g., 12-30 m/s and 6-23 m/s, respectively), while C and Group IV fibers have a slow conduction velocity (e.g., 0.3-1.5 m/s and <2.5 m/s, respectively). Part of the difference in conduction velocity between Aδ and Group III fibers and C and Group IV fibers is attributed to the fact that Aδ and Group III fibers are myelinated (i.e., they are thinly sheathed in myelin, which is an electrically insulating material), while C and Group IV fibers are not. Accordingly, stimulation of Aδ and Group III fibers elicits an early, rapid pain that is sharp in nature, while stimulation of C and Group IV fibers elicits a later, prolonged pain that is dull and achy in nature. In other words, Aδ and Group III fibers typically conduct impulses that signal the initial perception of pain from extreme pressure, severe temperature, and/or injury, while C and Group IV fibers conduct impulses that signal a prolonged aching experience following the initial perception of pain. Conduction of signals by Aδ and Group III fibers is most susceptible to blockage by depriving the affected area of adequate oxygen supply, and conduction of signals by C and Group IV fibers is most susceptible to blockage by anesthetizing the affected area.

Returning to FIG. 2, unmyelinated C fibers are the most prevalent fibers in a typical human sensory nerve (~80%), with Aδ and Aβ fibers being equally less prevalent with one another (~10% each). The small-diameter C fibers have the longest refractory period, with the larger diameter Aδ and Aβ fibers having shorter refractory periods. The differences in those refractory periods are presumably a direct result of the quantity of ion channels available per surface area of each fiber. Smaller diameters also yield higher charge thresholds and require a longer duration of stimulus depolarization to generate an action potential at the fiber. For example, in the absence of pharmacologic interventions or pathologic conditions, a range of sine waves from 0.01-2.0 mA can be applied to a C fibers at a frequency of 5 Hz to generate action potentials at those fibers; a range of sine waves from 0.03 to 2.2 mA can be applied to Aδ fibers at a frequency of 250 Hz to generate action potentials at those fibers; and a range of sine waves from 0.22 to 6.0 mA can be applied to Aβ fibers at a frequency of 2,000 Hz to generate action potentials at those fibers. A sine wave is preferably used because of that waveform's frequency-dependent rate of depolarization.

Because smaller diameters yield longer refractory periods, that sine wave stimulus can be applied for different periods of time so as only to affect a specific nerve fiber. For example, the Aβ fibers can respond to a short duration (e.g, ~0.25 ms) of sine wave stimulation applied at a frequency of 2,000 Hz while the smaller-diameter fibers (i.e., Aδ and C fibers) require a significantly longer period (e.g., ~100 ms for a C fiber) of sine wave stimulation to respond. And the Aβ fibers will re-polarize more quickly than the frequencies (e.g., 5 Hz and 250 Hz) used to generate an action potential in the smaller-diameter fibers (i.e., Aδ and C fibers) can depolarize the Aβ fibers. In other words, smaller-diameter fibers do not achieve their threshold action potentials over shorter durations, and larger-diameter fibers do not achieve their threshold action potentials at lower frequencies. Together those factors allow selective responses to be separately evoked from Aβ, Aδ, and C fibers using different frequencies (Hz), intensities (mA), and durations (ms) of electrical stimulation. Accordingly, that type of targeted electrical stimulation is hereinafter referred to as "neuro-specific" electrical stimulation and the device that allows a user to select between those targets is hereinafter referred to as "neuro-selective" stimulator.

An important advantage of using electrical stimulation to assess pain and target specific sensory nerve fibers rather than traditional injury-producing stimulation (e.g., thermal, chemical, and mechanical stimuli) is that such electrical stimulation bypasses the peripheral nociceptors and stimulates the targeted nerve fiber directly. As a result, receptor-dependent processes such as accommodation (i.e., intensification of stimulus needed to elicit the same response) and habituation (i.e., reduced or inhibited responsiveness during repeated stimulation) do not occur. Thus, use of electrical stimulation not only allows the characterization of the nociceptive pathways carried by the individual sensory nerve types, it also allows for repeated testing of nerve specific fibers without inducing injury.

In addition, the present invention utilizes electrical stimulation below that considered or perceived as painful or noxious to patients to determine their respective SDTs. Such "sub-noxious" neuro-specific stimulation is applied by generating electrical stimulation with an intensity that is large enough to achieve the targeted nerve fiber's threshold action potential but small enough that the patient does not consciously perceive a feeling of pain in response to that electrical stimulation. Accordingly, sub-noxious electrical stimulation applied at neuro-specific frequencies (e.g., 5 Hz and 250 Hz) can thereby be used to achieve threshold action potentials for Aδ and C fibers, separately, without the patient actually perceiving pain.

B. Cortical Activity Monitoring

In addition to the receptors and nerve fibers discussed above, the somatosensory system further comprises the anterior cingulate cortex (Brodmann Areas 24, 32, & 33), the primary somatosensory cortex (Brodmann Areas 3, 1, & 2), the secondary somatosensory cortex (Brodmann Area 5), the insular cortex (Brodmann Areas 13 & 14), the dorsolateral prefrontal cortex (Brodmann Areas 9 & 46), and the parietal cortex (Brodmann Area 7). Each of those cortical regions of the brain plays a different role within the somatosensory system. For example, the primary somatosensory cortex (S1) processes intensity information for tactile and nociceptive stimuli, and the dorsolateral prefrontal cortex (DLPFC) encodes attentional and emotional information for tactile and nociceptive stimuli. Accordingly, those cortical regions of the brain can be monitored to measure a patient's response to such stimuli. Such monitoring techniques include near infrared spectroscopy (NIRS) and electroencephalography (EEG).

NIRS is a an optical emission and absorption technique that assesses hemodynamic changes in the cortical regions of a patient's by estimating cerebral oxygenation using infrared light to penetrate living tissue and measuring the amount of infrared light absorbed by tissue chromophores, such as hemoglobin (i.e., oxyhemoglobin [$O_2Hb$], deoxyhemoglobin [HHb], and total hemoglobin [$HbT=O_2Hb+HHb$]) and cytochrome aa3 (i.e., oxidized cytochrome aa3). Increased oxygenation represents an increase in regional blood flow, which, in the brain, has been demonstrated to correlate to increases in cortical activity. Light in the near-infrared spectrum (i.e., light with a wavelength of 700-1000 nm) is able to penetrate tissue far enough to illuminate cortical regions of the brain, such as the primary somatosensory cortex and the dorsolateral prefrontal cortex. Oxyhemoglobin, deoxyhemoglobin, and oxidized cytochrome aa3 each have different absorption spectra in the near-infrared spectrum, just as they do in the visible spectrum. Accordingly, NIRS can be used to measure the concentration hemoglobin and oxidized cytochrome aa3 in those cortical regions as well as the hemoglobin-oxygen saturation (i.e., $StO_2=O_2Hb/tHb$) and cytochrome aa3 redox status (i.e., reduction in oxidized cytochrome aa3) in those cortical regions.

Figure 3A:
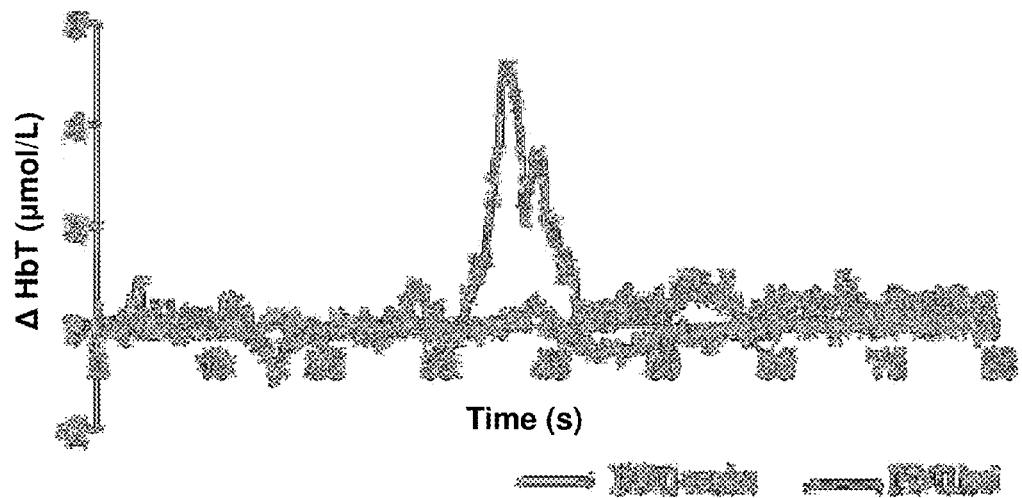
FIGS. 3A and 3B are graphs that illustrate changes in total hemoglobin plotted over time that indicate a response to stimuli as measured with NIRS.
Figure 3B:
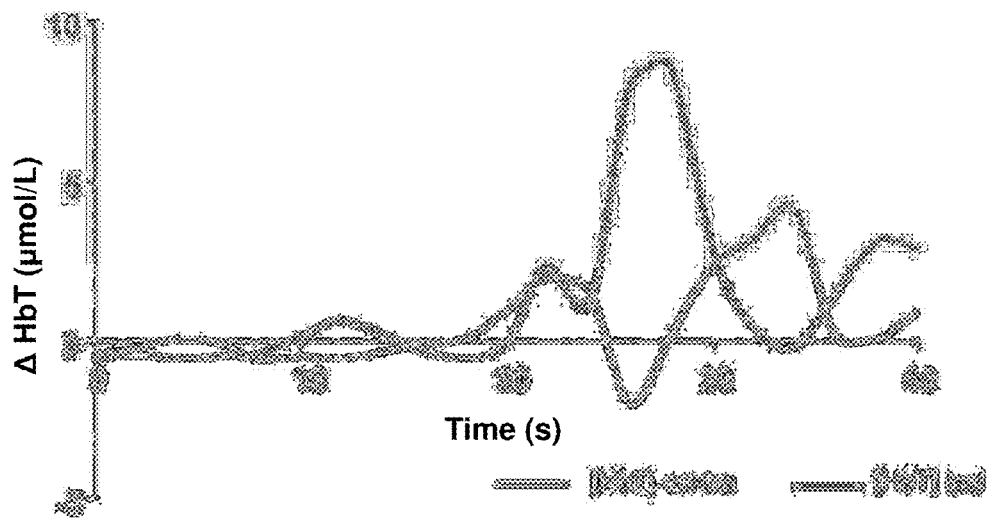

As FIGS. 3A and 3B illustrate, those measurements can be used to monitor hemodynamic responses to a specific stimuli in the cortical regions of a patient's brain. FIG. 3A includes data obtained from a 5-week old preterm neonate (i.e., postmenstrual age of 30 weeks) using a sampling frequency of 6 Hz (i.e., 6 measurements were taken per second), and FIG. 3B includes data obtained from a 5-week old preterm neonate (i.e., postmenstrual age of 34 weeks) using a sampling frequency of 2 Hz (i.e., 2 measurements were taken per second). In those figures, changes in total hemoglobin are plotted over time using NIRS measurements taken at the primary somatosensory cortex. Stimulation was applied to the patients at twenty seconds (20 s), causing a significant increase in total hemoglobin measured at the contralateral primary somatosensory cortex just moments later. Because that increased tissue oxygenation represents an increase in regional blood flow in the contralateral primary somatosensory cortex (i.e., an increase in activity in the contralateral primary somatosensory cortex), FIGS. 3A and 3B demonstrate the effectiveness of NIRS in measuring a patient's response to specific stimuli, particularly in neonates and infants.

NIRS is particularly suited for measuring pain in neonates and infants because, as discussed above, the true experience of pain includes an emotional component. And neonates and infants quickly adapt their behavioral response to painful stimuli, rendering conventional pain assessment apparatus/methods ineffective. Thus, NIRS is particularly suited for measuring pain in neonates and infants because it is able to separate the emotional component of pain from the nociceptive component, such as via a comparison of hemodynamic changes measured at the primary somatosensory cortex (nociceptive) and the dorsolateral prefrontal cortex (emotional).

EEG is a biopotential measurement technique that assesses brain activity by placing electrodes on the skin of a patient's skull and measuring the intensity and pattern of excitatory and inhibitory potentials generated by the brain. The EEG signal is often divided into different frequency bands: Delta (<4 Hz), Theta (4-8 Hz), Alpha (8-12 Hz), Beta (13-30 Hz); and Gamma (>30 Hz). Activation of a cortical area is characterized by a decrease in the amplitude of EEG oscillations in the Alpha band and an increase in the amplitude of EEG oscillations in the Gamma band. Accordingly, EEG can be used to measure neural and hemodynamic activity in different cortical regions of the brain, such as the primary somatosensory cortex and the dorsolateral prefrontal cortex.

Figure 4A:
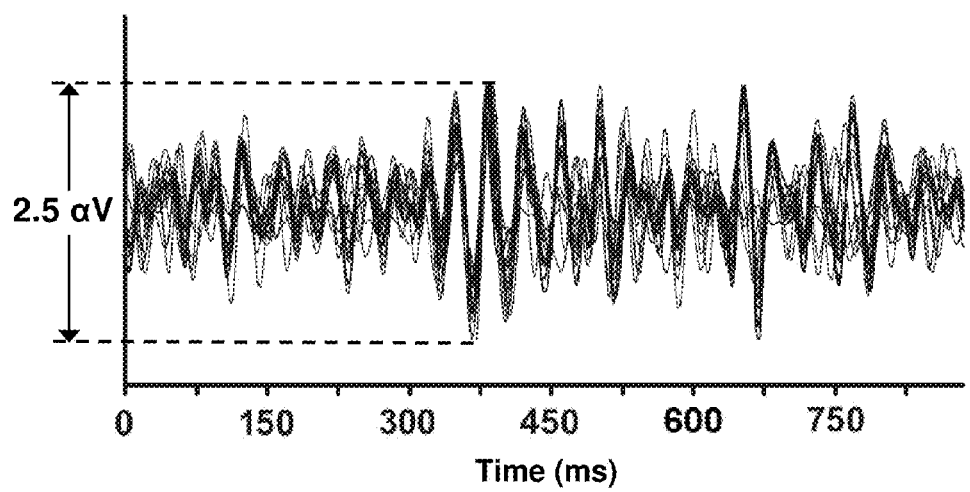
FIG. 4A is a graph that illustrates EEG oscillations plotted over time.
Figure 4B:
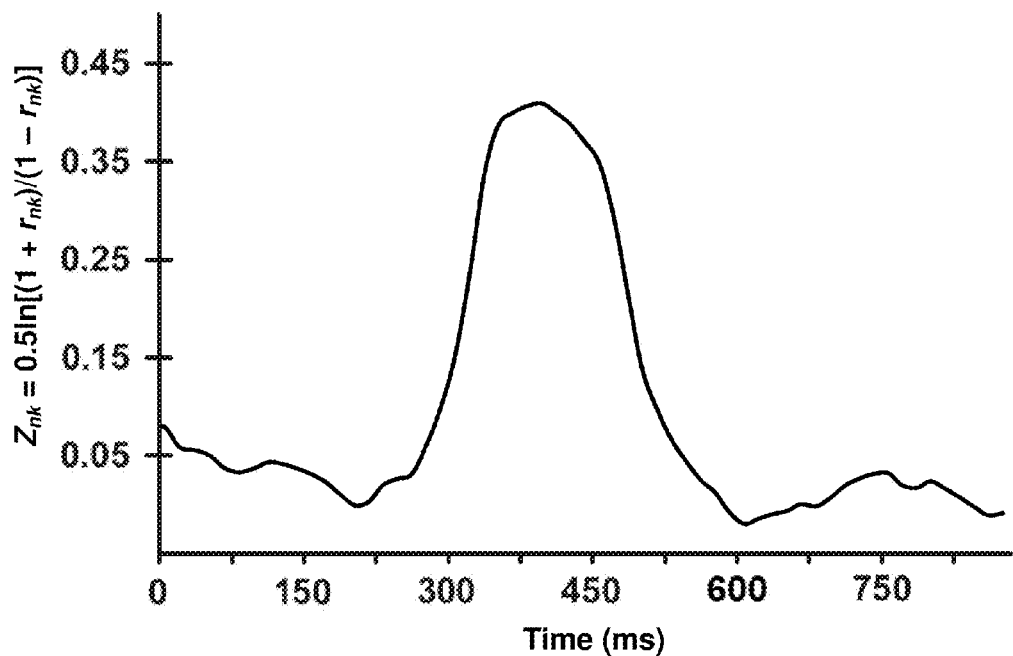
FIG. 4B is a graph that illustrates Fisher's Z values for the EEG oscillations of FIG. 4A plotted over time that indicate a response to stimuli as measured with EEG.

As FIGS. 4A and 4B illustrate, those measurements can also be used to monitor cortical responses to different stimuli. FIGS. 4A and 4B include data obtained from a 19-30 year-old patient using EEG measurements taken at the $C_z$ scalp location in the 38-72 Hz frequency range of the Gamma band. FIG. 4A plots the EEG oscillations over time, and FIG. 4B plots the Fisher's Z values (i.e., $Z_{nk}=0.5 \ln [(1+r_{nk})(1-r_{nk})]$) of those EEG oscillations over time. Correlation analyses were used to statistically estimate the covariance of the EEG oscillations in subsets of EEG sweeps and the resulting correlation coefficients (i.e., $r_{nk}$) were converted into Fisher's Z values to provide a normalized measure of oscillation responses during the time interval of analysis. A more detailed description of that normalization method is provided in Maltseva, I., et al., "Alpha oscillations as an indicator of dynamic memory operations—anticipation of omitted stimuli", *Int. J. Psychophysiology*, vol. 36(3), 185-197

(2000), the contents of which are hereby incorporated by reference in their entirety as if fully set forth herein.

In FIGS. 4A and 4B, stimulation was applied to the patient at three hundred seventy-five milliseconds (375 ms), causing a significant increase in Z values for the EEG oscillations measured near the primary somatosensory cortex at approximately the same time. Because those increased Z vales represent activation of the primary somatosensory cortex (i.e., an increase in activity in the primary somatosensory cortex), FIGS. 4A and 4B also demonstrate the effectiveness of EEG in measuring a patient's response to certain stimuli, particularly in neonates and infants. EEG is particularly suited for measuring pain in neonates and infants for reasons similar to those discussed above with respect to NIRS. It is also particularly suited for measuring pain in neonates and infants because their brains, due to their immature nature, only express a few well-defined set of patterns, making those patterns easier to recognize with EEG.

Although the foregoing examples describe taking NIRS and EEG measurements at or near the primary somatosensory cortex, those measurements may alternatively or additionally be taken in other cortical regions, such as the dorsolateral prefrontal cortex and occipital cortex. As discussed above, the primary somatosensory cortex processes intensity information for tactile and nociceptive stimuli, and the dorsolateral prefrontal cortex encodes attentional and emotional information for tactile and nociceptive stimuli. In other words, activity in the primary somatosensory cortex is more closely associated with the nociceptive component of pain and activity the dorsolateral prefrontal cortex is more closely associated with the emotional component of pain. Activity in the dorsolateral prefrontal cortex is also associated with analgesia, both placebo and analgesic induced. And activity in the occipital cortex generally does not mirror pain-related activity in the primary somatosensory cortex and the dorsolateral prefrontal cortex. Accordingly, measurements at the occipital cortex can be used as a control for measurements at the primary somatosensory cortex and/or the dorsolateral prefrontal cortex. Moreover, NIRS and/or EEG measurements can be taken at both the primary somatosensory cortex and the dorsolateral prefrontal cortex to help distinguish between the nociceptive and emotional components of pain and/or between drug-induced and emotion-induced analgesia. Either NIRS or EEG can be used at both locations, NIRS may be used at one location and EEG used at another location, or both EEG and NIRS can be used at both locations. The latter configuration can be used to obtain duplicate and, therefore, more reliable measurements.

C. Algometer

The present invention utilizes a novel combination of neuro-specific electrical stimulation and cortical activity monitoring, wherein the neuro-specific electrical stimulation is directly correlated to the monitored cortical activity in real time to provide an objective measurement of pain intensity and analgesia. It uses those measurements to provide an objective quantification of pain (e.g., a pain score, an SDT value, etc.), to provide an objective measurement of the effect of currently used analgesics and other pain interventions, to provide an objective measurement of the efficacy and dose-response relationships of newly developed and/or investigational drugs and other interventions targeted for the management of pain, to identify the onset of tolerance and/or analgesic-induced toxicity, and to provide an objective characterization of pain (e.g., nociceptive pain, neuropathic pain, hyperalgesia, allodynia, etc.). That functionality is provided by a single device, hereinafter referred to as a "human algometer", or just "algometer".

Figure 5:
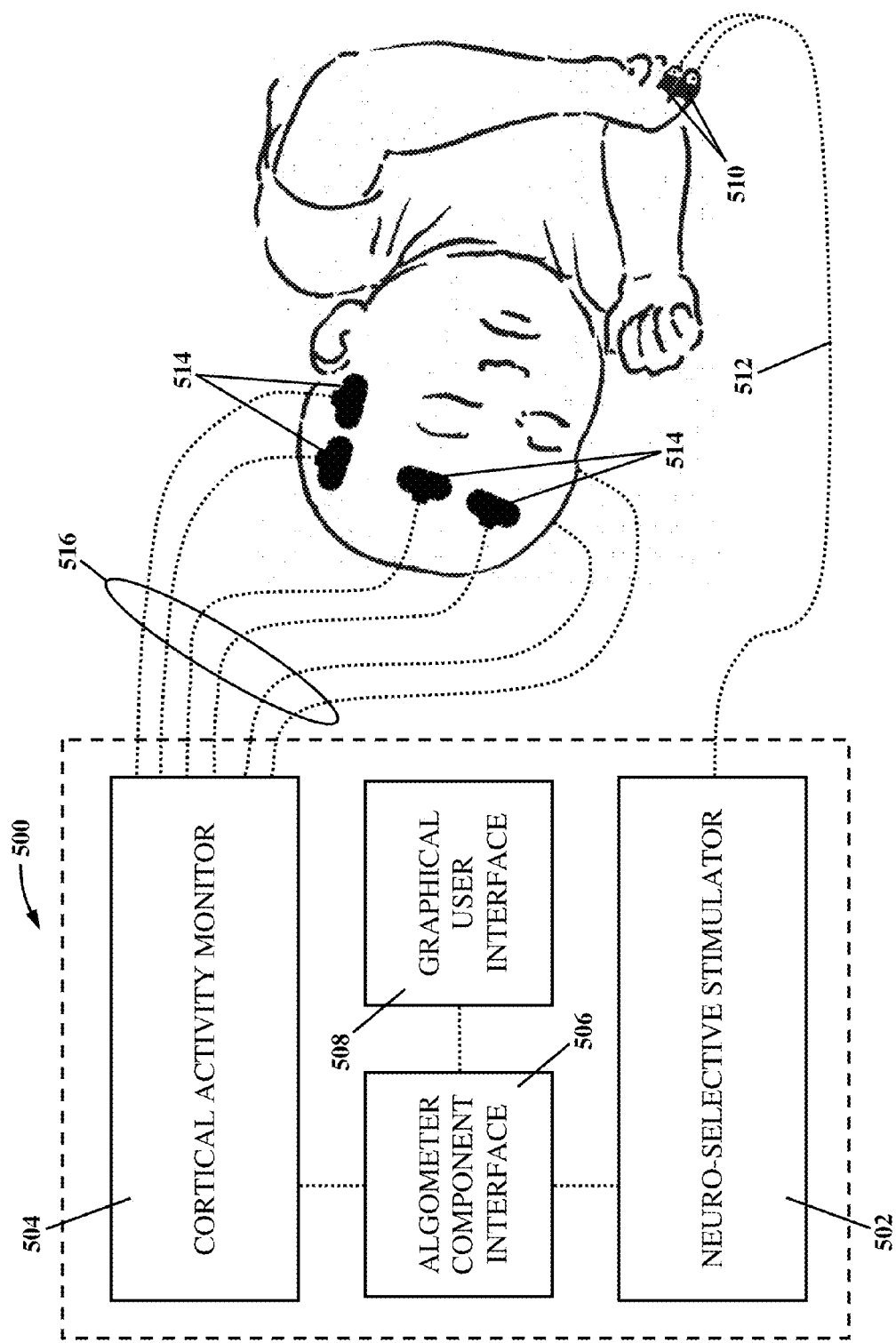
FIG. 5 is a schematic diagram that illustrates an algometer according to anon-limiting embodiment of the present invention.

FIG. 5 illustrates an example of a human algometer 500 according to a non-limiting embodiment of the present invention. That algometer 500 includes a neuro-selective stimulator 502, a cortical activity monitor 504, a component interface 506, and a graphical user interface 508. The neuro-selective stimulator 502 is configured to apply neuro-specific stimulation to specific nerve fibers (e.g., $A\beta$, $A\delta$, and C fibers) using specific voltages and currents applied at neuro-specific frequencies (i.e., 2000, 250, and 5 Hz). The cortical activity monitor 504 is configured to monitor cortical activity based on hemodynamic and/or neurophysiological responses to the neuro-specific electrical stimulation generated by the neuro-selective stimulator 502 and/or to other forms of stimulation. The component interface 506 is configured to control both the neuro-selective stimulator 502 and the cortical activity monitor 504, to integrate the functionality of those two components 502 and 504, and to store the data obtained with those two components 502 and 504. And the graphical user interface 508 is configured to receive and transmit data that is input by a user to control the neuro-selective stimulator 502 and the cortical activity monitor 504 and to analyze and display the data that is measured, sampled, and stored with those three components 502, 504, and 506.

Although the algometer 500 illustrated in FIG. 5 is described primarily in terms of NIRS, EEG can be used instead of or in addition to NIRS without departing from the spirit of the present invention. Moreover, other suitable forms of cortical activity monitoring (e.g., functional Magnetic Resonance Imaging (fMRI), near infrared imaging (NIRI), etc.) can be used instead of or in addition to NIRS and/or EEG without departing from the spirit of the present invention. But because the equipment required to perform NIRS and EEG is generally less cumbersome than that utilized for other forms of cortical activity monitoring, and due at least to the features of NIRS and EEG discussed above, the algometer 500 of the present invention preferably utilizes NIRS and/or EEG.

i. Neuro-Selective Stimulator 502

Figure 6:
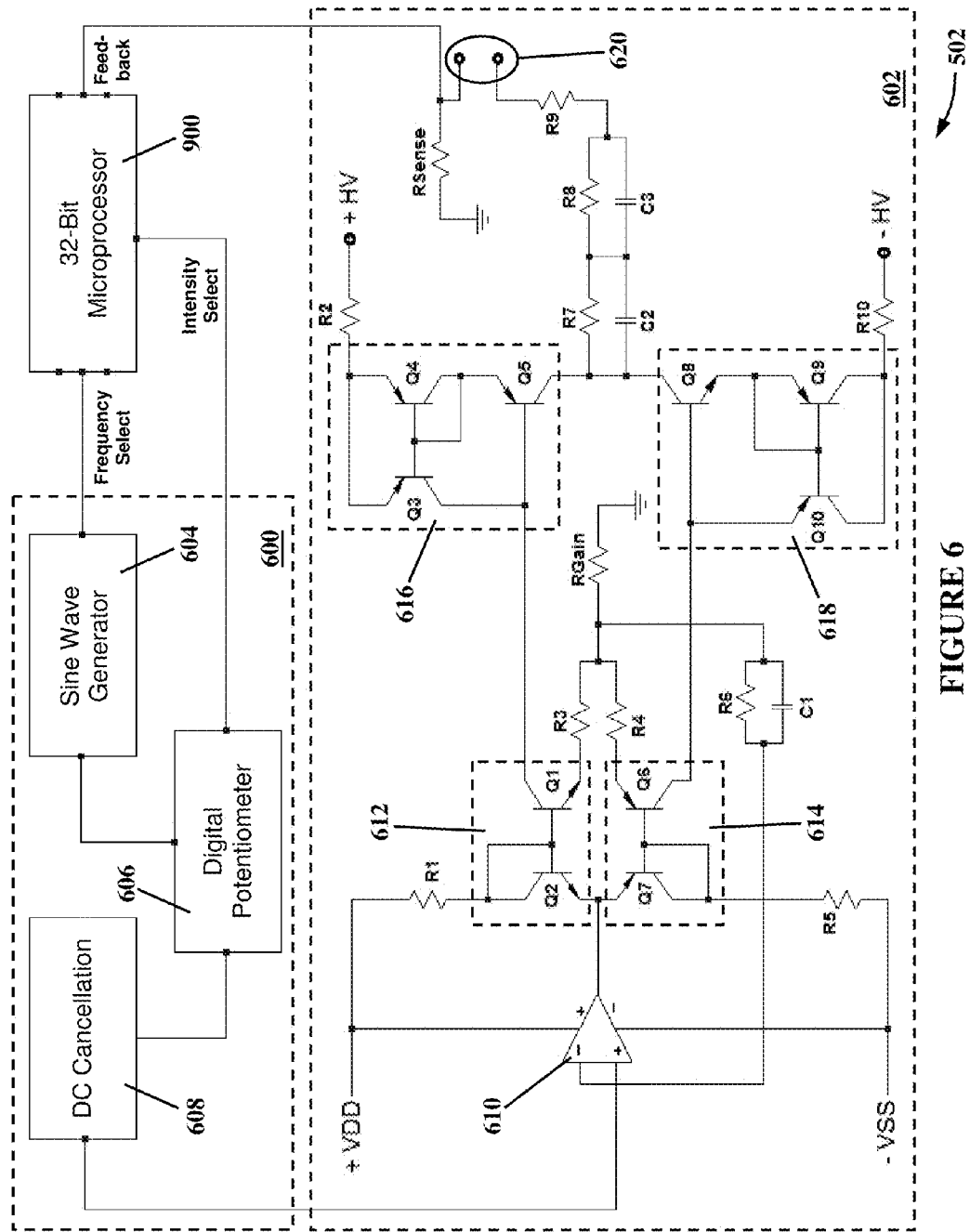
FIG. 6 is a schematic diagram that illustrates the neuroselective stimulator component of an algometer according to a non-limiting embodiment of the present invention.

As FIG. 6 illustrates, the neuro-selective stimulator 502 includes a low-voltage circuit 600 and a high-voltage circuit 602. The low-voltage circuit 600 and the high-voltage circuit 602 are both connected to a microprocessor 900 (FIG. 9) in the component interface 506. The low-voltage circuit 600 includes a sine wave generator circuit 604, a digital potentiometer circuit 606, and a DC cancellation circuit 608. And the high-voltage circuit 602 includes a precision non-inverting operational amplifier (op-amp) 610, a first current mirror 612, a second current mirror 614, a first high voltage current source 616, a second high voltage current source 618, and electrode inputs/outputs 620. The low-voltage circuit 600 generates a pure AC sine wave signal that is converted to a current-based signal by the high-voltage circuit 602.

In more detail, the microprocessor 900 is connected to the sine wave generator circuit 604, which includes a low-power Direct Digital Synthesis (DDS) programmable waveform generator integrated circuit (IC). The microprocessor 900 sends commands ("Frequency Select" in FIG. 6) to the sine wave generator circuit 604 for generating different signal frequencies (e.g., 5, 250, and 2000 Hz) that correspond to the stimulus required to activate different nerve fibers (e.g., C, $A\delta$, and $A\beta$ fibers). The microprocessor 900 also sends a crystal referenced 1 mega-Hertz (MHz) clocking signal to the sine wave generator circuit 604, which the sine wave generator circuit 604 uses to generate the requisite sine wave signals with a frequency accuracy of ±10 milli-Hertz (mHz).

The sine wave generator circuit 604 and the microprocessor 900 are both connected to the digital potentiometer circuit 606. The sine wave generator circuit 604 sends the sine wave it generates to the digital potentiometer circuit 606. And the microprocessor 900 sends commands ("Intensity Select" in FIG. 6) to the digital potentiometer circuit 606 that correspond to different signal amplitudes, which are used by a voltage divider at the digital potentiometer circuit 606 to apply different signal amplitudes to the sine waves generated by the sine wave generator circuit 604. Those signal amplitudes are precisely controlled by the microprocessor 900 so they can be used by the high-voltage circuit 602 to generate currents with different intensities (e.g., 0.5, 0.85, and 2.3 mA) that correspond to the stimulus required to activate different nerve fibers (e.g., C, Aδ, and Aβ fibers). The maximum intensity generated by the high-voltage circuit 602 is set such that only sub-noxious stimulus is applied to a patient (i.e., an intensity large enough to achieve the targeted nerve fiber's threshold action potential but small enough that the patient does not consciously perceive a feeling of pain).

The digital potentiometer circuit 606 is connected to the DC cancellation circuit 608 and sends the signals generated with the input from the microprocessor 900 and the sine wave generator circuit 604 to the DC cancellation circuit 608. The DC cancellation circuit 608 removes the DC components from those signals, thereby producing a pure AC signal with the desired frequency and amplitude. The resulting voltage-based signal is then sent to the high-voltage circuit 602 for conversion into to a current-based signal.

The DC cancellation circuit 608 of the low-voltage circuit 600 is connected to the non-inverting input of the non-inverting op-amp 610 of the high-voltage circuit 602. A precision gain resistor $R_{Gain}$ is connected to the inverting input of the non-inverting op-amp 610 through a resistor-capacitor combination $R_6/C_1$. The DC cancellation circuit 608 sends the voltage-based sine wave signal generated with the input from the digital potentiometer circuit 606 to the non-inverting op-amp 610 while the gain resistor $R_{Gain}$ is used to control the gain of the high-voltage circuit 602. The non-inverting op-amp 610 preferably has input bias currents of less than a few pico-amperes (pA), and the gain resistor $R_{Gain}$ preferably has a resistance of approximately 10 ohms.

The non-inverting op-amp 610 is connected to the first transistors $Q_2$ and $Q_7$ of the first and second current mirrors 612 and 614, respectively. And the second transistors $Q_1$ and $Q_6$ of the first and second current mirrors 612 and 614 are connected to the gain resistor $R_{Gain}$ and the non-inverting input of the non-inverting op-amp 610 through resistors $R_1$ and $R_5$, respectively. The first and second transistors $Q_2$ and $Q_1$ of the first current mirror 612 are NPN transistors, and the first and second transistors $Q_7$ and $Q_6$ of the second current mirror 614 are PNP transistors.

The second transistors $Q_1$ and $Q_6$ of the first and second current mirrors 612 and 614 are connected to the first transistors $Q_3$ and $Q_{10}$ of the first and second high voltage current sources 616 and 618, respectively, and outputs of the first and second current mirrors 612 and 614 are sent to the first and second high voltage current sources 616 and 618, respectively. High voltage sources $+H_v$ (e.g., +400 V) and $-H_v$ (e.g., −400 V) are connected to the second transistors $Q_4$ and $Q_9$ of the first and second high voltage current sources 616 and 618 through resistors $R_2$ and $R_{10}$, respectively. And the third transistors $Q_5$ and $Q_8$ of the first and second high voltage current sources 616 and 618 are connected to the electrode inputs/outputs 620 through a resistor $R_9$ and a pair of resistor-capacitor combinations $R_7/C_2$ and $R_8/C_3$ in series. The first, second, and third transistors $Q_3$, $Q_4$, and $Q_5$ of the first high voltage current source 616 are PNP transistors, and the first, second, and third transistors $Q_{10}$, $Q_9$, and $Q_8$ of the second high voltage current source 618 are NPN transistors.

Together, the components of the high-voltage circuit 602 operate as a voltage-to-current converter capable of generating current stimuli with intensities of 10 mA and greater.

The electrode inputs/outputs 620 of the high-voltage circuit 602 are connected to a current measuring resistor and to the microprocessor 900. The outputs of the first and second current mirrors 612 and 614 are combined and sent to the electrode inputs/outputs 620 via the pair of resistor-capacitor combinations $R_7/C_2$ and $R_8/C_3$ to provide further DC cancellation and to compensation for changes in a patient's skin impedance. And the resulting current that is applied to a patient is measured through the measuring resistor $R_{Sense}$ and sent back to the microprocessor 900 for fine adjustment ("Feedback" in FIG. 6). For example, the microprocessor 900 will automatically reduce the intensity of the current if it is measured to be higher than the current required to target the desired nerve fiber and/or higher than the threshold current for producing sub-noxious stimulation. In that way, the low-voltage circuit 600 provides precise control of the frequency and amplitude of the desired signal, and the high-voltage circuit 602 provides precise voltage-to-current conversion.

The electrode inputs/outputs 620 are connected to electrodes 510 through corresponding electrode cables 512. See, e.g., FIG. 5. The electrodes 510 provide a consistent, distortion free interface between the neuro-selective stimulator 502 and a patient's skin. The electrodes 510 are preferably gold plated and paired together using a flexible spreader to standardize the distance between them. The electrodes are also preferably cupped to accommodate electrode gel for maintaining a consistent output current density for reliable, repeatable results. The electrode cables 512 are lightweight lead wires that are terminated with spring loaded molded portions configured to resiliently hold the electrodes 510. The electrodes 510 and electrode cables 512 may be reusable or disposable and designed for single-use only. The algometer 500 is configured to operate using commercially available electrodes 510 and electrode cables 512, which helps reduce the manufacturing and operational costs of the algometer 500.

ii. Cortical Activity Monitor 504

Figure 7:
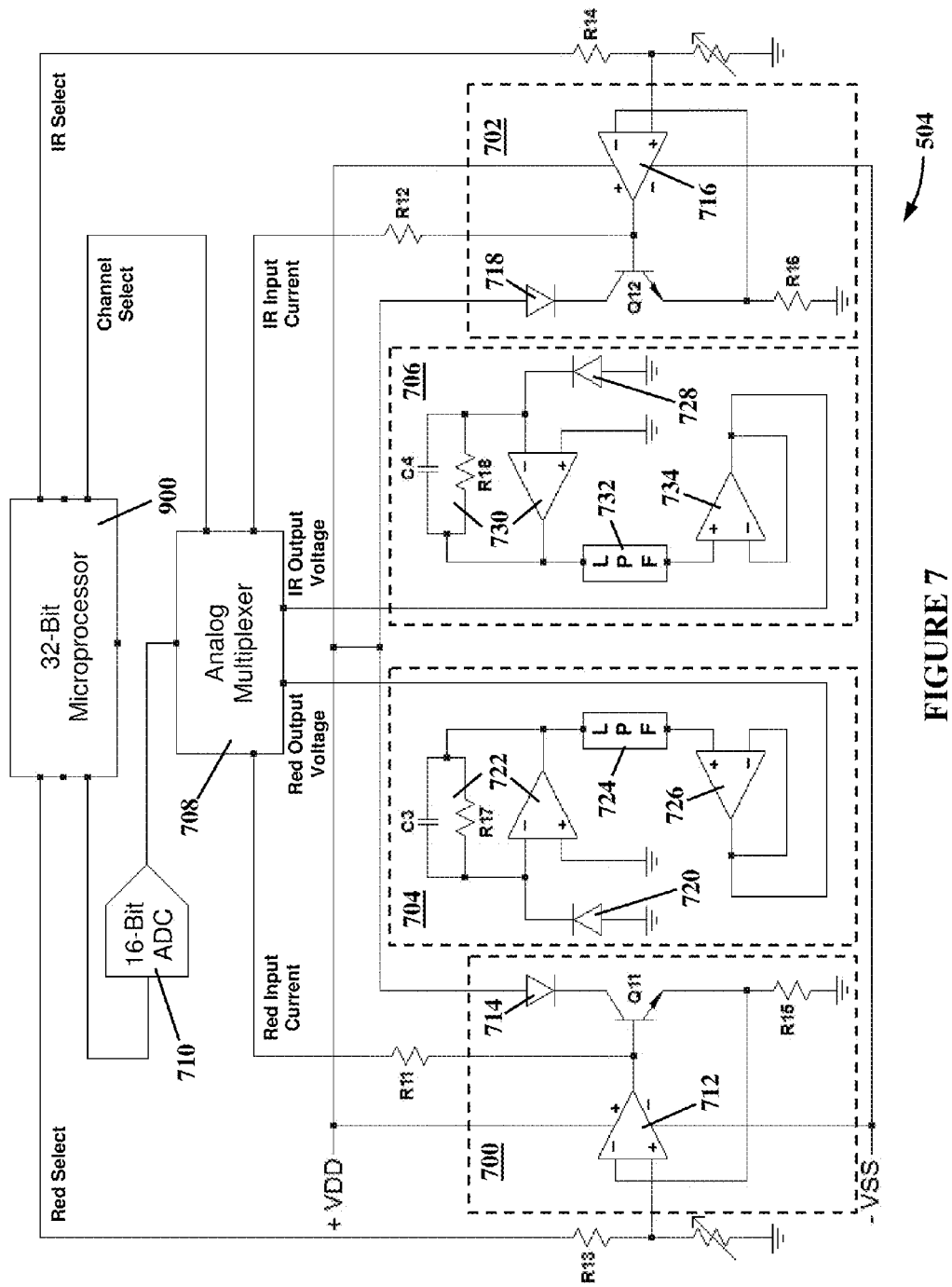
FIG. 7 is a schematic diagram that illustrates the cortical activity monitor component of an algometer according to a non-limiting embodiment of the present invention.

As FIG. 7 illustrates, the cortical activity monitor 504 includes a first current driver circuit 700, a second current driver circuit 702, a first photo-detector circuit 704, a second photo-detector circuit 706, an analog multiplexer 708, and a high-resolution 16-bit analog-to-digital converter (ADC) 710. Like the low-voltage circuit 600 and the high-voltage circuit 602 of the neuro-selective stimulator 502, the different subcomponents 700-710 of the cortical activity monitor 504 are connected to the microprocessor 900. The first current driver circuit 700 includes a first precision non-inverting op-amp 712, a red light emitter 714, and a transistor $Q_{11}$; the second current driver circuit 702 includes a second precision non-inverting op-amp 716, an IR light-emitter 718, and a transistor $Q_{12}$; the first photo-detector circuit 704 includes a first photo-detector diode 720, a first trans-impedance op-amp 722, a first low-pass filter (LPF) 724, and a first voltage follower op-amp 726; and the second photo-detector circuit 706 includes a second photo-detector diode 728, a second trans-impedance op-amp 730, a second LPF 732, and a second voltage follower op-amp 734. Red light and IR light are emitted from the red and IR light emitters 714 and 718 and the reflected light is detected by the first and second photo-detector diodes 720 and 728, respectively.

In more detail, the microprocessor 900 (FIG. 9) of the component interface 506 is connected to the non-inverting input of the first non-inverting op-amp 712 and the non-inverting input of the second non-inverting op-amp 716 through resistors $R_{13}$ and $R_{14}$, respectively. The microprocessor 900 generates the requisite current excitation level for the red and IR light emitters 718 by selecting those resistors $R_{13}$ and $R_{14}$ to receive current ("Red Select" and "IR Select" in FIG. 7, respectively) in an alternating manner. The resulting voltage drops across those resistors $R_{13}$ and $R_{14}$ are converted into currents by the first and second current driver circuits 700 and 702, and those currents cause the red light emitter 714 and IR light emitter 718 to emit red light and IR light, respectively, in an alternating manner. The microprocessor 900 controls the rate of emission and the delay between the red light emitter 714 and IR light emitter 718 as required to measure hemodynamic changes in the cortical regions of a patient's brain. For example, light emissions may be repeated at a rate of 125 Hz with a duty cycle of 25% for each light emitter 714 and 718.

The microprocessor 900 is also connected to the multiplexer 708, which is connected to outputs of the first and second current driver circuits 700 and 702 through resistors $R_{11}$ and $R_{12}$, respectively. The microprocessor 900 is also connected to the multiplexor 708 through the ADC 710. The multiplexer 708 receives the outputs of the first and second current driver circuits 700 and 702 ("Red Input Current" and "IR Input Current" in FIG. 7, respectively), samples those outputs, and forwards them to the ADC 710. The ADC 710 converts the analog current outputs from the first and second current driver circuits 700 and 702 into digital signals and sends those signals to the microprocessor 900, where they are analyzed and temporarily stored. For example, the microprocessor 900 will determine the length, frequency, and intensity of each signal, identify those signals as separate stimulus cycles, and temporarily store that data on RAM before sending it to the graphical user interface 508 for further processing. Those digital signals represent the input currents to the red and IR light emitters 714 and 718, which correspond to the amount of red and IR light emitted by the red and IR light emitters 714 and 718, respectively.

The outputs of the first and second photo-detector circuits 704 and 706 are also connected to the multiplexer 708. As the red and IR light that is emitted by the red and IR light emitters 714 and 718 propagates subcutaneously in a patient's skull, it is differentially absorbed at one end of the path of propagation by skin, brain tissues, and hemoglobin and cytochrome aa3 in the cerebral vasculature of the patient's brain. At the other end of the path of propagation, the red and IR light that is not absorbed by genetic material is received by the first and second photo-detector diodes 720 and 728. Each of the first and second photo-detector diodes 720 and 728 converts the received light into an electrical signal by generating a current that is proportional to the amount of light that it receives (i.e., the amount of photons it absorbs). That current is received by the corresponding trans-impedance op-amp 722 or 730 and transformed into a voltage. Because that current can be very small with a very small signal to noise ratio, the first and second trans-impedance op-amps 722 and 730 each preferably have extremely large input impedance with input currents in the pico-ampere (pA) range, which provides very precise amplification.

The output voltages of the first and second trans-impedance op-amps 722 and 730 are sent through the first and second LPFs 724 and 732, respectively, so as to further remove noise from those output voltages. The order of the first and second LPFs 724 and 732 and the position of their poles are selected to remove noise while maintaining the integrity of the resulting signal at the cortical activity monitor's 504 operating frequency (e.g., 125 Hz). The output voltages then pass through the first and second voltage follower op-amps 726 and 734 to eliminate loading effects. The multiplexer 708 receives the resulting output voltages ("Red Output Voltage" and "IR Output Voltage" in FIG. 7, respectively), samples them, and forwards them to the ADC 710.

The ADC 710 converts the analog voltage outputs from the first and second photo-detector circuits 704 and 706 into digital signals and sends those signals to the microprocessor 900, where they are analyzed and temporarily stored. For example, the microprocessor will collect fifty data points from each photo-detector circuit 704 and 706, average those data points, and temporarily store them in RAM before sending them to the graphical user interface 508 for further processing. Those digital signals represent the amount of current generated at the first and second photo-detector diodes 720 and 728, which correspond to the amount of red and IR light received by the first and second photo-detector diodes 720 and 728, respectively. And by comparing the amount of red and IR light received by first and second photo-detector diodes 720 and 728 with the amount of red and IR light emitted by the red and IR light emitters 714 and 718, the microprocessor 1000 (FIG. 10) of the graphical user interface 508 is able to measure the amount of hemodynamic change that occurs over time in the cortical regions of a patient's brain.

The red light emitter 714, the IR light emitter 718, the first photo-detector diode 720, and the first photo-detector diode 728 are provided as part of a single NIRS sensor 514 that is connected to the algometer 500 through a corresponding sensor cable 516. See, e.g., FIG. 5. The NIRS sensor 514 is configured to couple to a patient's skin tissue adjacent to a cortical region of the patient's brain so that red and IR light can be propagated into those cortical regions by the red and IR light emitters 714 and 718 and so that the reflected red and IR light can be received by the first and second photo-detector diodes 720 and 728, respectively. The red light emitter 714 is configured to emit red light with a wavelength that corresponds to the absorption spectra of deoxyhemoglobin (i.e., 730-775 nm); the IR light emitter 718 is configured to emit IR light with a wavelength that corresponds to the absorption spectra of deoxyhemoglobin (e.g., 850-900 nm); the first photo-detector diode 720 is configured to generate a current that is proportional to the amount of light it receives in the red light wavelength spectrum (i.e., 600-750 nm); and the second photo-detector diode 728 is configured to generate a current that is proportional to the amount of light it receives in the IR light spectrum (i.e., 750-1000 nm). In the alternative, one or both of the first and second photo-detector diodes 720 and 728 may be configured to generate a current based on the amount of light they receive in both of those wavelength spectrums (i.e., 600-1000 nm).

The red light emitter 714 and the IR light emitter 718 may include separate semiconductor diode elements, or dies, that emit light at different wavelengths within their respective wavelength spectrums. For example, the IR light emitter 718 may include one die that emits light at wavelengths centered around 910 nm and another that emits light at wavelengths centered around 810 nm. Similarly, a single light-emitting diode (LED) may include both the red light emitter 714 and the IR light emitter 718 as well as their respective dies. For example, a single LED may include a die for the red light emitter 714 that emits light at wavelengths centered around 730 nm and an IR light emitter 718 according to the previous example. When more than two dies are provided to generate light at more than two wavelengths in that manner, one or more additional driver circuits 700 or 702 will be provided in the cortical activity monitor 504 to generate the required excitation currents to cause the extra die or dies to emit that light.

Regardless of the number of different wavelengths of light the red light emitter 714 and the IR light emitter 718 are configured to generate, the red light emitter 714 and the IR light emitter 718 and their respective dies are preferably provided in a single LED. And the first and second photo-detector diodes 720 and 728 are preferably configured to generate a current based on the amount of light they receive in both of the red and IR wavelength spectrums (i.e., 600-1000 nm). In that way, both the LED and the first and second photo-detector diodes 720 and 728 can be used interchangeable to generate and receive light at all of the available wavelengths, which provides greater flexibility when configuring the NIRS sensor 514.

Figure 8A:
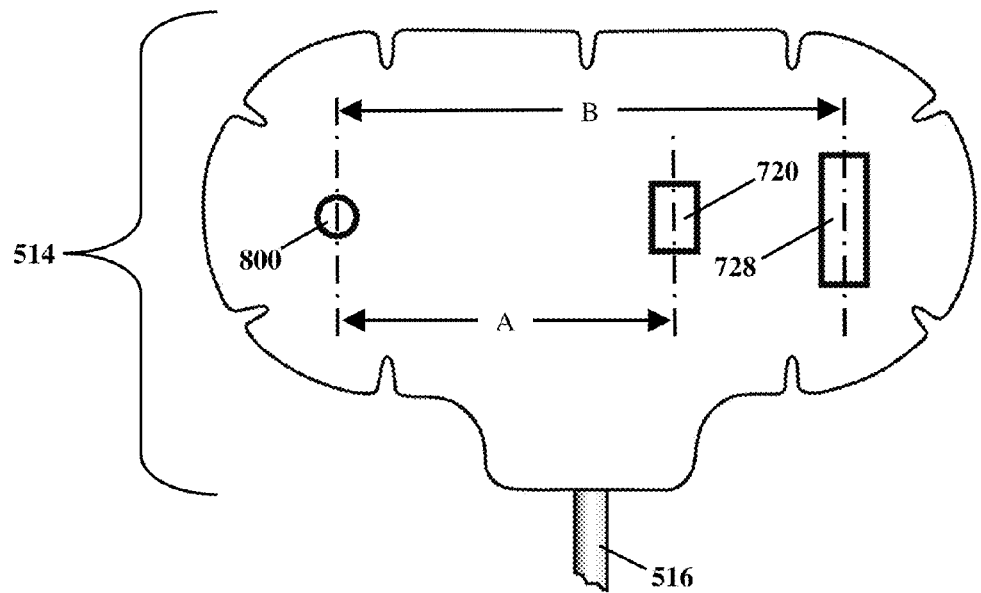
FIG. 8A is drawing that illustrates a single emitter/dual detector NIRS sensor according to a non-limiting embodiment of the present invention.

FIG. 8A illustrates an exemplary NIRS sensor 514 that includes a single LED 800 with includes both the red light emitter 714 and the IR light emitter 718 provided therein, as well as their respective dies. Because the mean penetration depth of photons is proportional to the distance between the emitting source and the receiving detector, the LED 800 is preferably placed a shorter distance A to the first photo-detector diode 720 than the distance B to the second photo-detector diode 728, wherein the second photo-detector diode 728 is preferably larger than the first photo-detector diode 720 to compensate for that larger distance B. That configuration creates two different propagation paths with two different path lengths—a short path from the red and IR light emitters 714 and 718 to the first photo-detector diode 720 and a longer path from the red and IR light emitters 714 and 718 to the second photo-detector diode 728. The shorter path measures hemodynamic changes within the skin, muscle, and bone of a patient's head while the longer path measures those hemodynamic changes as well as hemodynamic changes in the cortical regions of the patient's brain. And the measurement ($M_A$) taken with the first photo-detector diode 720 via the short path can then be subtracted from the measurement ($M_B$) taken with the second photo-detector diode 728 via the long path to isolate the measurement ($M_{Cortical}$) at the cortical region of the patient's brain (i.e., $M_B - M_A = M_{Cortical}$).

Figure 8B:
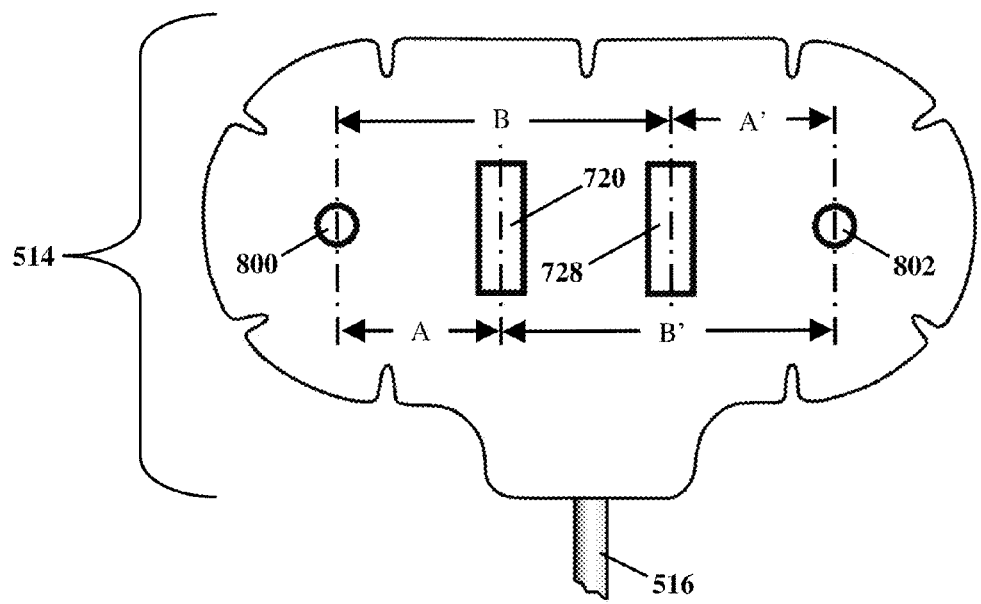
FIG. 8B is drawing that illustrates a dual emitter/dual detector NIRS sensor according to a non-limiting embodiment of the present invention.

Unfortunately, any variation in the skin, muscle, and/or bone between the locations at which the first and second photo-detector diodes 720 and 728 are placed can introduce error into those measurements. Accordingly, the NIRS sensor 514 preferably includes a second LED 802 that also includes both a red light emitter 714 and an IR light emitter 718 as well as their respective dies. As FIG. 8B illustrates, that configuration allows two pair of propagation paths with different path lengths to be created, wherein the first LED 800 is placed a shorter distance A to the first photo-detector diode 720 than the distance B to the second photo-detector diode 728 and the second LED 802 is placed a shorter distance A' to the second photo-detector diode 728 than the distance B' to the first photo-detector diode 720. Because both the first and second photo-detector diodes 720 and 728 absorb photons from both a short and long path, they are both preferably large enough to operate effectively for both of those path lengths.

The measurement ($M_A$) taken with the first photo-detector diode 720 via the shorter path to the first LED 800 is subtracted from the measurement ($M_B$) taken with the second photo-detector diode 728 via the longer path to the first LED 800 and the measurement ($M_A'$) taken with the second photo-detector diode 728 via the shorter path to the second LED 802 is subtracted from the measurement ($M_B'$) taken with the first photo-detector diode 720 via the longer path to the second LED 802 to isolate the measurement ($M_{Cortical}$) at the cortical region of the patient's brain (i.e., $(M_B - M_A) + (M_B' - M_{sA}') = M_{Cortical}$). In that way, the dual emitter/dual detector configuration of FIG. 8B accounts for variations in the skin, muscle, and/or bone between the locations at which the first and second photo-detector diodes 720 and 728 are placed. And, as described in U.S. Pat. No. 7,865,223 to Bernreuter, the spacing between the first and second LEDs 800 and 802 and the first and second photo-detector diodes 720 and 728 can be modified or changed as required to optimize measurements at different tissue depths. Moreover, as also described in that patent, the additional measurements provided by that dual-emitter/dual detector configuration can be taken alternately at three different wavelengths to further remove surface effects. The disclosure of that patent is hereby incorporated by reference in its entirety as if fully set forth herein.

Regardless of the configuration of the NIRS sensors 514, they may be reusable or disposable and designed for single-use only. The sensor cables 516 may be provided separately from or integrated with the NIRS sensors 514 and may be reusable or disposable. For example, the NIRS sensors 514 of FIGS. 8A and 8B may be disposable with reusable sensor cables 516, disposable with integrated disposable sensor cables 516, or reusable with integrated reusable sensor cables 516. The algometer 500 is configured to operate using commercially available NIRS sensors 514 and sensor cables 516, which helps reduce the manufacturing and operational costs of the algometer 500.

Although only one NIRS sensor 514 is discussed in detail above, the algometer 500 is configured to utilize multiple NIRS sensors 514 at different locations on a patient's head as required to measure hemodynamic changes at different cortical regions (e.g., the occipital cortex, the primary somatosensory cortex, the secondary somatosensory cortex, the insular cortex, the dorsolateral prefrontal cortex, the parietal cortex, etc.) on different patients (e.g., adults, children, infants, neonates, lab animals, etc.). And although only two current driver circuits 700 and 702 and two photo-detector circuits 704 and 706 are discussed in detail above, the algometer 500 includes a corresponding number of current driver circuits 700 and 702 and photo-detector circuits 704 and 706 to the number of NIRS sensors 514 and dies in their respective LEDs 800 and 802. In FIG. 5, for example, six NIRS sensors 514 are provided that each have two LEDs 800 and 802 with three dies. Accordingly, the cortical activity monitor 504 in FIG. 5 has thirty-six current driver circuits (6 NIRS sensors×2 LEDs/NIRS sensor×3 dies/LED×1 current driver circuit/die=36 current driver circuits) and twelve photo-detector circuits (6 NIRS sensors×2 photo-detector circuits/NIRS sensor=12 photo-detector circuits).

iii. Component Interface 506

Figure 9:
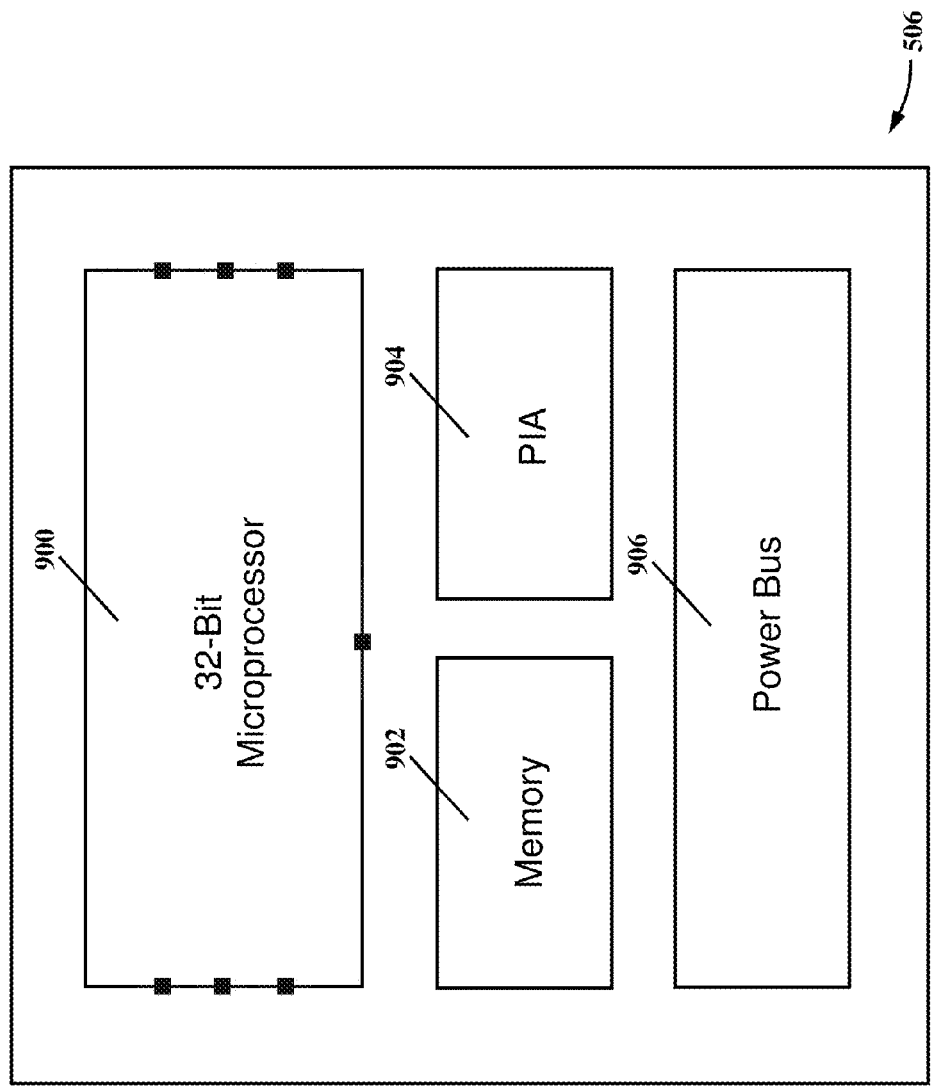
FIG. 9 is a block diagram that illustrates the component interface of an algometer according to a non-limiting embodiment of the present invention.

As FIG. 9 illustrates, the component interface 506 includes the microprocessor 900 that is shared by the neuro-selective stimulator 502 and the cortical activity monitor 504. As discussed above, the microprocessor controls the neuro-selective stimulator 502 and the cortical activity monitor 504 and integrates the functionality of those components 502 and 504. The component interface 506 also includes memory 902, a peripheral interface adapter (PIA) 904, and a power bus 906. The memory 902 stores the software that is executed by the microprocessor 900 and the data that is generated with the neuro-selective stimulator 502 and the cortical activity monitor 504; the PIA 904 provides a connection via which the microprocessor 900 can electronically communicate with external devices; and the power bus 906 provides a common source of power for operating the microprocessor 900, the neuro-selective stimulator 502, and the cortical activity monitor 504.

In more detail, the memory 902 includes read-only memory (ROM) and random-access memory (RAM). ROM is a non-volatile memory chip where the essential system instructions (i.e., basic input/output system (BIOS) instructions) are permanently stored. Those instructions control the operations and interactions of the neuro-selective stimulator 502 and the cortical activity monitor 504. And RAM is a volatile memory chip where portions of those instructions are temporarily stored before they are carried out by the microprocessor 900. The microprocessor 900 may also temporarily store other data on the RAM, such as the data generated with the neuro-selective stimulator 502 and the cortical activity monitor 504. Such data can be temporarily stored on the RAM, for example, prior to sending it to the graphical user interface 508 for further processing.

The PIA 904 is a specialized interface chip that provides parallel in/out interfacing capability for the microprocessor 900, thereby allowing the algometer 500 to be connected to peripherals, such as printers or monitors. It may also allow the algometer 500 to be connected to a hospital's central monitoring system. When the graphical user interface 508 is provided as a separate computing device from the algometer 500 (e.g., a personal computer, laptop computer, tablet computer, etc.), the PIA 904 will provide interfacing capability with that device. Accordingly, the memory 902 will include the requisite instructions stored on the ROM for facilitating one or more of those types of interfaces. And the algometer 500 will include an appropriate connection port for connecting to such external devices (e.g., an RS-232 connection, an RJ45 connection, a universal serial bus (USB) connection, a coaxial cable connection, etc.).

Although not illustrated, the component interface 506 includes a set of specialized signal generating chips that are controlled by the microprocessor 900. For example, the component interface 506 may include a digital-to-analog converter (DAC) for converting digital signals into voltage or current as required to perform various tasks, such as generating the requisite current excitation level to cause the red light emitter 714 and IR light emitter 718 to emit red light and IR light, respectively. Those chip sets serve to alleviate the microprocessor 900 from the burden of digital signal generation, thereby freeing the microprocessor 900 to perform signal processing of the data generated with the neuro-selective stimulator 502 and the cortical activity monitor 504. Moreover, they can be used to perform tasks that would otherwise be performed by complex circuits in the algometer, such the first and second current driver circuits 700 and 702, thereby allowing the size and complexity of the algometer 500 to be significantly reduced.

iv. Graphical User Interface

Figure 10:
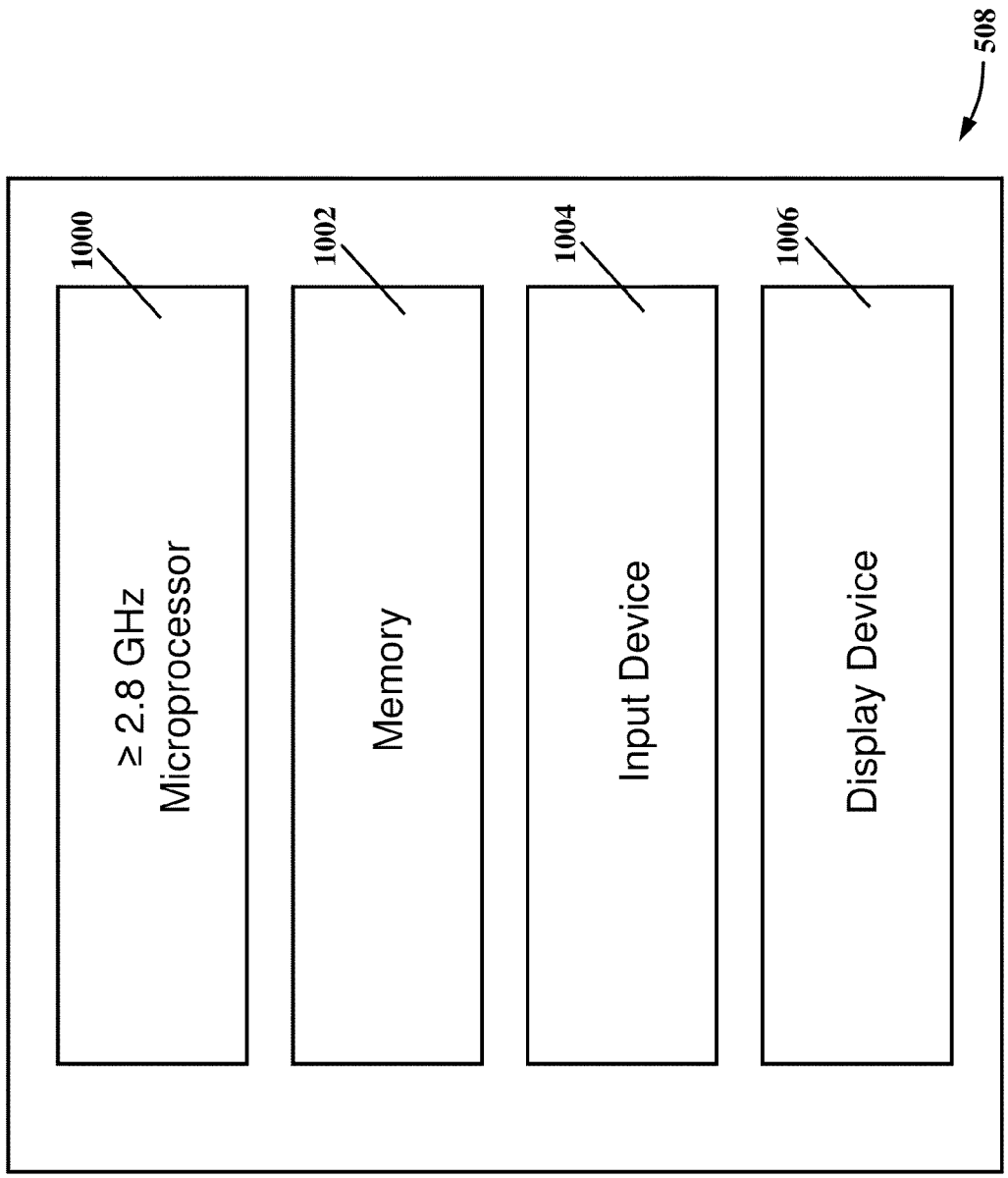
FIG. 10 is a block diagram that illustrates the graphical user interface component of an algometer according to a non-limiting embodiment of the present invention.

As FIG. 10 illustrates, the graphical user interface 508 includes its own microprocessor 1000 and its own memory 1002. It also includes a user input device 1004, and a display device 1006. The microprocessor 1000 controls the overall operation of the algometer 500; the memory 1002 stores data and software used to by the microprocessor 1000 to control the overall operation of the algometer 100; the input device 1004 receives input from a user to set the parameters for performing different tests with different patients; and the display device 1006 displays the data input into and generated by the various components 502-508 of the algometer 500. Those subcomponents 1000-1006 of the graphical user interface 508 work together to coordinate and automate stimulation algorithms and response detection at a patient's somatosensory cortex and other cortical regions of the patient's brain, and to perform data capture, storage, and processing.

In more detail, the microprocessor 1000 communicates with the memory 1002, input device 1004, and display device 1006 of the graphical user interface 508 and the microprocessor of the component interface 506 as required to generate, gather, and analyze pain data. The microprocessor 1000 receives input from a user via the input device 1004 and selects which algorithms to perform from the software stored on the memory 1002. For example, a user can utilize the input device 1004 (e.g., a keyboard, a touchscreen, a mouse, etc.) to select the type of analysis that the algometer 500 will perform (e.g., determining SDTs, determining a pain score, monitoring the effects of an analgesic, etc.) and the parameters that will define any variables that will affect that analysis (e.g., patient age, type of NIRS sensor 514 being used, location of NIRS sensors 514, type of electrodes 510 being used, location of electrodes 510, type of EEG electrode 1100 being used, location of EEG electrodes 1100, etc.). The microprocessor 1000 will then initiate the selected type of analysis by sending a command to the microprocessor 900 of the component interface 506, which will then generate the appropriate electrical stimulation with the neuro-selective stimulator 502 and generate the appropriate light emissions with the cortical activity monitor 504.

As the microprocessor 900 of the component interface 506 identifies the separate stimulus cycles generated by the neuro-selective stimulator 502 and averages the data points collected by the cortical activity monitor 504, it will temporarily store that data on its RAM and periodically send that data back to the microprocessor 1000 of the graphical user interface 508 in packets for further processing and extended storage. Those packets of data will identify the frequency and intensity of the electrical stimulation applied by the electrodes 510, the current levels at which red and IR light are emitted by the red and IR light emitters 714 and 718, and the currents detected by the photo-detector diodes 720 and 728. And the microprocessor 900 of the component interface 506 will send those packets of data to the microprocessor 1000 of the graphical user interface 508 after each of a series of concurrent loops of electrical stimulation and NIRS and/or EEG are performed. The microprocessor 1000 of the graphical user interface 508 will then analyze that data using its own processing loop based on the type of analysis selected and the parameters input via the input device 1004. Those loops are described in more detail below with respect to the algometer software.

The microprocessor 1000 dynamically displays the results of that analysis at the display device 1006 in a relevant numerical (e.g., a recorded SDT value, a calculated pain score, etc.), verbal (e.g., a written outcome, a written warning, etc.), and/or graphical (e.g., a plot of pain response, a pain scale graph, etc.) format. The microprocessor 1000 may also dynamically display the values of the electrical stimulation applied with the neuro-selective stimulator 502 (e.g., frequency, intensity, cycle time, etc.) and/or the values of hemodynamic and/or neurophysiological changes measured with the cortical activity monitor 504 (e.g., threshold oxygenation and/or electrical activity values, somatosensory oxygenation and/or electrical activity values, change in oxygenation and/or electrical activity values, etc.) in a similar manner. In that way, a user (e.g., a qualified healthcare provider) can monitor a patient's physiological response to the electrical stimulation in a meaningful numerical, verbal, and/or graphical format, which allows that user to make accurate clinical decisions regarding pain and pain management. In fact, the algometer 500 may even be connected to other medical devices (e.g., a drug-dispensing system) and programmed to control those medical devices based on the patient's physiological response (e.g., decreasing or increasing dosing from the drug-dispensing machine).

The microprocessor 1000 stores the data received from the neuro-selective stimulator 502 and the cortical activity monitor 504 (via the microprocessor 900 of the component interface 506) and the results of the analysis in the memory 1002 of the graphical user interface 508. That data (e.g., stimulus frequency and intensity, hemodynamic and/or neurophysiological change, pain scores, SDT values, etc.) is associated with the specific patient on whom the analysis was performed, codified, and stored in a secure manner for later retrieval or communication into an electronic health record (EHR) system and/or for subsequent review. That data is associated with a specific patient based on the data input into the graphical user interface 508 via the input device 1004, which can include the patient's name and/or identifying information. And that data can be communicated to an EHR system wirelessly via a wireless interface, using a connection made via the PIA 904 of the component interface 506, using a connection made via a PIA (not shown) in the graphical user interface 508, or using a portable storage medium (e.g., a rewritable disk, a flash drive, etc.).

The graphical user interface 508 includes a separate microprocessor 1000 from the component interface 506 to further alleviate the burden of complex processing at the microprocessor 900 of the component interface 506, thereby freeing that microprocessor 900 to primarily function for processing the data generated with the neuro-selective stimulator 502 and the cortical activity monitor 504. Moreover, it allows the graphical user interface 508 to be provided as a separate computing device (e.g., a personal computer, a laptop computer, a tablet computer, etc.) from the neuro-selective stimulator 502, the cortical activity monitor 504, and the component interface 506. In that configuration, the graphical user interface 508 could be connected to the neuro-selective stimulator 502, the cortical activity monitor 504, and the component interface 506 via the PIA 904 of the component interface 506, thereby allowing the algometer 500 to operate with any of a wide variety of different computing devices serving as the graphical user interface 508.

Similarly, any of the different components of the algometer 500 (i.e., neuro-selective stimulator 502, the cortical activity monitor 504, the component interface 506, and the graphical user interface 508), or subcomponents thereof (e.g., current driver circuits 700 and 702, photo-detector circuits 704 and 706, memory 1002, input device 1004, display device 1006, etc.), may also be provided as separate, stand-alone devices. Moreover, any of those components 502-508, or subcomponents 600, 602, 700-710, 902-906, and 1002-1006, can be in wireless data communication with each other via a wireless interface. For example, the current driver circuits 700 and 702, the photo-detector circuits 704 and 706, a wireless communicator, and an independent power source may be provided in or near an NIRS sensor 514 so that the NIRS sensor 514 can operate independently of and in wireless data communication with the other subcomponents 708 and 710 of the cortical activity monitor 504, thereby eliminating the need for sensor cables 516 between the algometer 500 and the NIRS sensors 514. Such wireless communications can occur via any suitable wireless technology (e.g., Wi-Fi, BLUETOOTH brand wireless technology, radio frequency (RF), etc.).

Because the microprocessor 1000 of the graphical user interface 508 performs more complex processing than the microprocessor 900 of the component interface 506, such as generating dynamic displays at the graphical user interface and executing the various process loops defined by the algometer software, it is preferably faster than the microprocessor 900 of the component interface 506 (e.g., >2.8 GHz). It also and preferably has at least 4 MB of cache memory and at least 4 GB of RAM to support fast processing. And because the memory 1002 of the graphical user interface stores data for a plurality of patients over different time frames, it preferably includes at least 100 GB of solid state data storage. Providing the memory 1002 as a solid state storage device increases process and storage cycles and reduces the chances of hard drive failure, as experienced with conventional spinning platen type hard drives D. Algometer Software The integrated components 502-506 of the algometer 500 can be used to (1) objectively quantify pain and the response to noxious and sub-noxious stimuli, (2) determine SDTs and/or pain scores in response to such stimuli and other clinically relevant stimuli, (3) monitor the analgesic effects of drugs and other pain interventions and the efficacy and dose-response relationships of newly developed and/or investigational drugs targeted for the management of pain, (4) determine the onset of tolerance to analgesic and other interventions, and (5) provide a diagnostic characterization of pain, all of which guide the overall management of pain in a patient. That functionality is controlled by the software stored on the memory 1002 of the graphical user interface 508. And the microprocessor 1000 executes the instructions on that software to perform the various tasks required to provide that functionality.

In more detail, the software includes stimulation algorithms that automate and coordinate simultaneous and self-consistent control of the sub-noxious electrical stimulation applied with the neuro-selective stimulator 502 and the hemodynamic and/or biopotential measurements performed with the cortical activity monitor 504. Which of those algorithms are executed by the microprocessor 1000 is determined by the data input by a user at the input device 1004 of the algometer 500. A user can not only select from among the four functions listed above, he or she can also choose such things as the nerve fiber that will be targeted (e.g., $A\beta$, $A\delta$, or C fibers), the length of time stimulation will be applied (e.g., 1 second, 10 seconds, 15 seconds, or 20 seconds, etc.), the location of the electrodes 510 (e.g., left arm, left leg, left foot, etc.), the location of the NIRS sensors 514 and/or EEG electrodes 1100 (e.g., the occipital cortex, the primary somatosensory cortex, the dorsolateral prefrontal cortex, etc.), the location of the patient's pain (e.g., left arm, left leg, left foot, etc.), the developmental stage (e.g., neonate, child, adult, etc.) and/or age of the patient (e.g., 30 weeks postmenstrual, 2-5 years, >65 years, etc.), weight of the patient (e.g., X pounds, 100-125 pounds, 125-150 pounds, etc.), sex of the patient (e.g., male or female), any pertinent physical/medical condition of the patient (e.g., hyperalgesia, opioid addiction, heart condition, etc.), and/or any current or intended therapeutic intervention (e.g., opioids, alpha-2 agonists, etc.).

Each of those selections can play a factor in how the neuro-selective stimulator 502 needs to apply neuro-specific electrical stimulation (i.e., the frequency and/or intensity of electrical stimulation may need to be adjusted slightly for certain patients) and how the cortical activity monitor 504 measures hemodynamic and/or neurophysiological responses (i.e., the location and/or type of NIRS sensors 514 and/or the wavelength of light may need to be different for certain patients, and/or the location and/or type of EEG electrodes 1100 and/or the frequency of electrical activity measured may need to be different for certain patients). And the algometer software includes algorithms that are configured to make the appropriate adjustments based on those various selections. For example, the distance between NIRS sensors 514 is determined by age, which determines, in part, the differential pathlength factor (DPF) and the algorithm used to measure hemodynamic changes at a given wavelength.

Figure 11A:
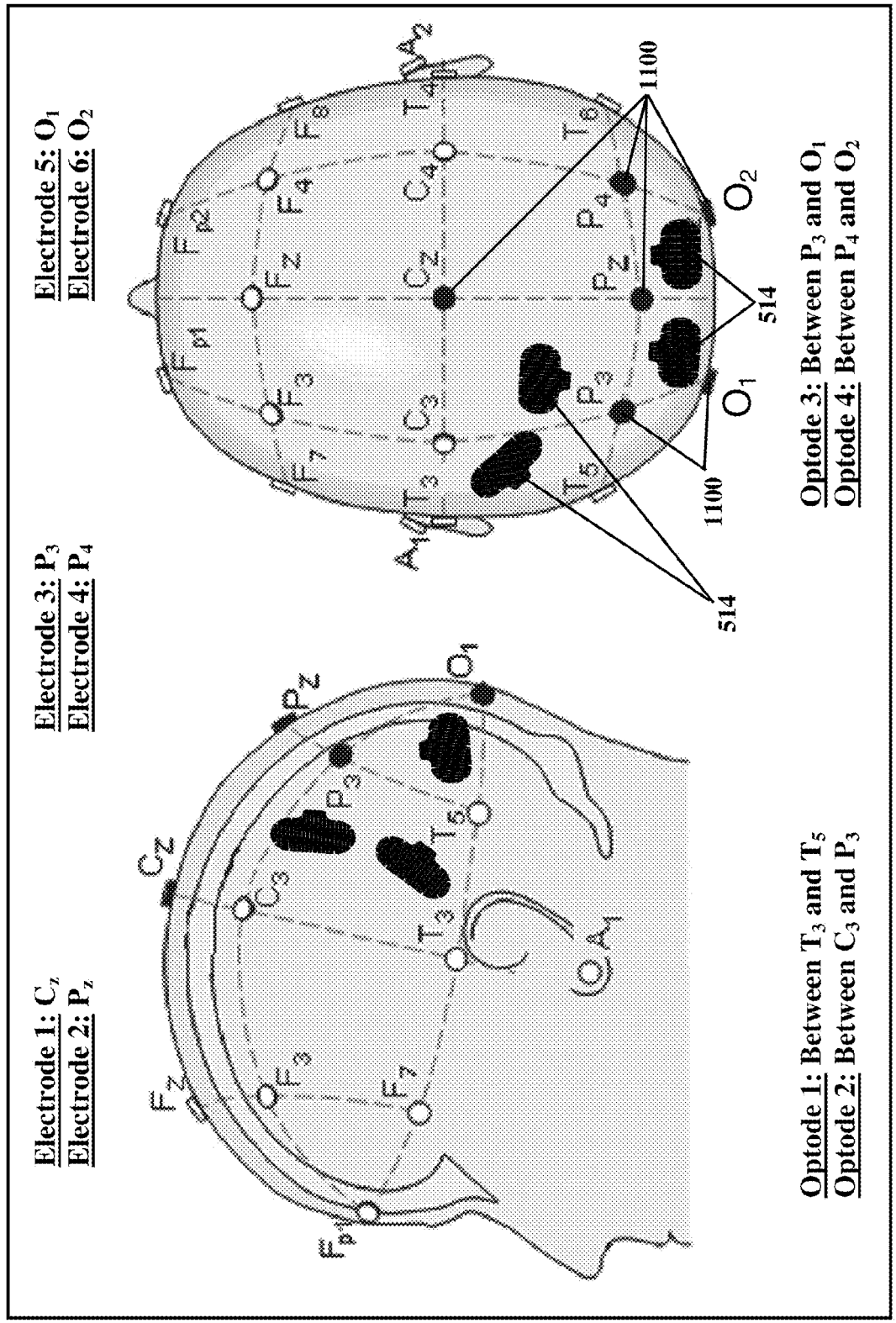
FIG. 11A is a drawing that illustrates an exemplary graphical display according to a non-limiting embodiment of the present invention.
Figure 11B:
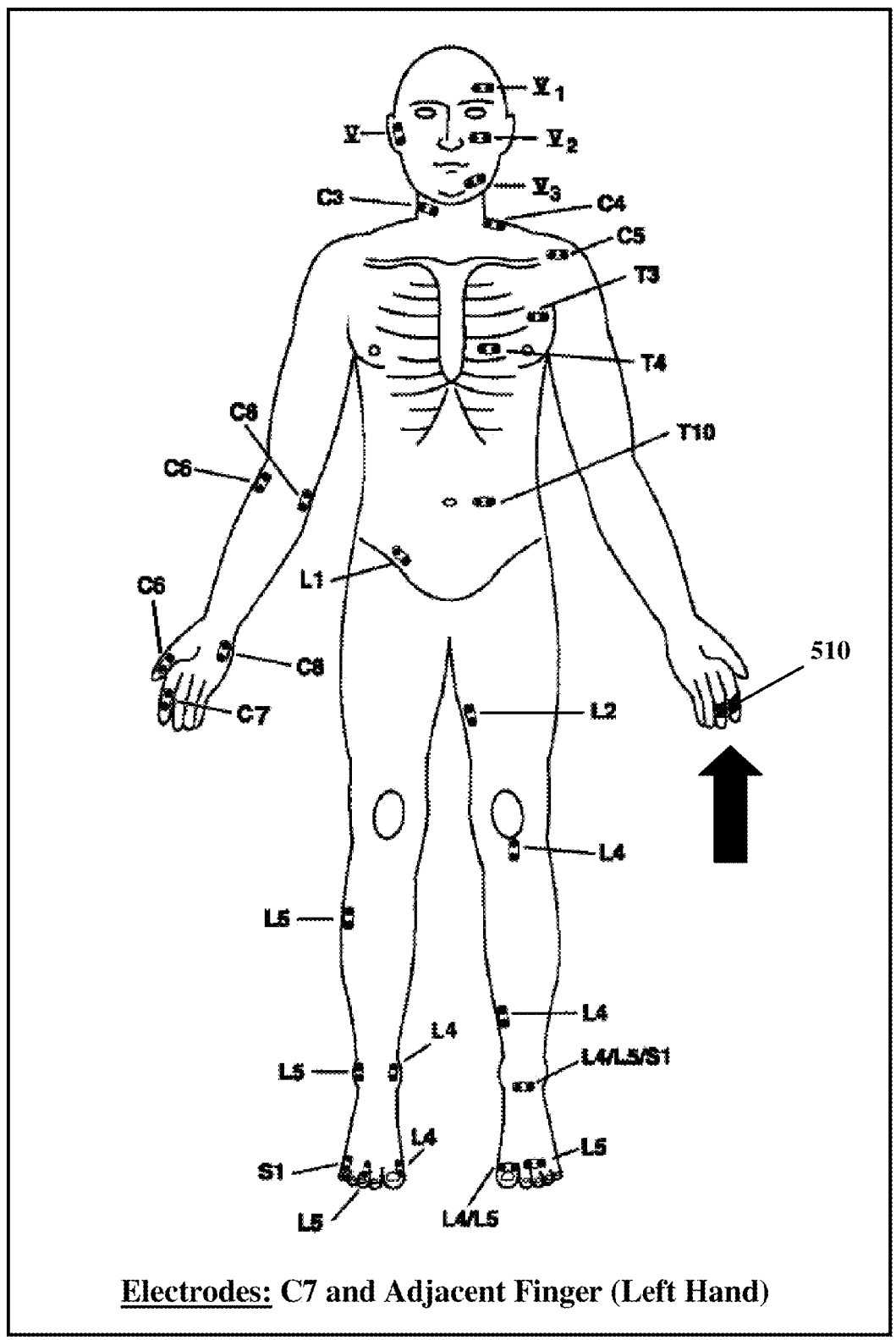
FIG. 11B is a drawing that illustrates an another exemplary graphical display according to another non-limiting embodiment of the present invention.

Some of those selections might result in instructions for the user being displayed on the display device 1006 of the algometer 500. For example, a user can select to monitor the effects of an opioid on an adult patient, which will result in the display device 1006 displaying instructions for placing the electrodes 510 on an extremity that is not the source of the patient's pain (e.g., segment C7), placing the NIRS sensors 514 on the occipital cortex and somatosensory cortex of the patient (e.g., between $T_3$ and $T_5$, between $C_3$ and $P_3$, between $P_3$ and $O_1$ and between $P_4$ and $O_1$), and/or placing EEG electrodes 1100 on the occipital cortex and somatosensory cortex of the patient (e.g., a $P_3$, $P_z$, $P_4$, $O_1$, and $O_2$). Those instructions can include a graphical display to better guide the user in placing the electrodes 510, NIRS sensors 514, and/or EEG electrodes 1100, such as the graphical displays illustrated in FIGS. 11A and 11B. And those selections will result in a current with a frequency of 5 Hz and an intensity of 0.50-0.80 mA chosen as the appropriate current to apply to that patient. That frequency and intensity are specific to C fibers, which are modulated by opioids. After the user has placed the electrodes 510, NIRS sensors 514, and/or EEG electrodes 1100 as instructed, he or she can instruct the algometer 500 to begin applying that neuro-specific electrical stimulation with the electrodes 510 and monitoring hemodynamic and/or neurophysiological responses with the NIRS sensors 514 and/or EEG electrodes 1100.

While neuro-specific electrical stimulation is being applied with the electrodes 510 and hemodynamic and/or neurophysiological responses are being monitored with the NIRS sensors 514 and/or EEG electrodes 1100, the microprocessor 1000 in the graphical user interface 508 will begin analyzing the data as it is received from the microprocessor 900 in the component interface 506. Those concurrent tasks are performed based on three separate process loops defined by the algometer software—a control/analysis loop, a stimulation loop, and a monitoring loop. The embedded structure of those loops is described hereinafter, starting from the outer-most loop and then followed by the inner loops.

i. Control/Analysis Loop

Figure 12:
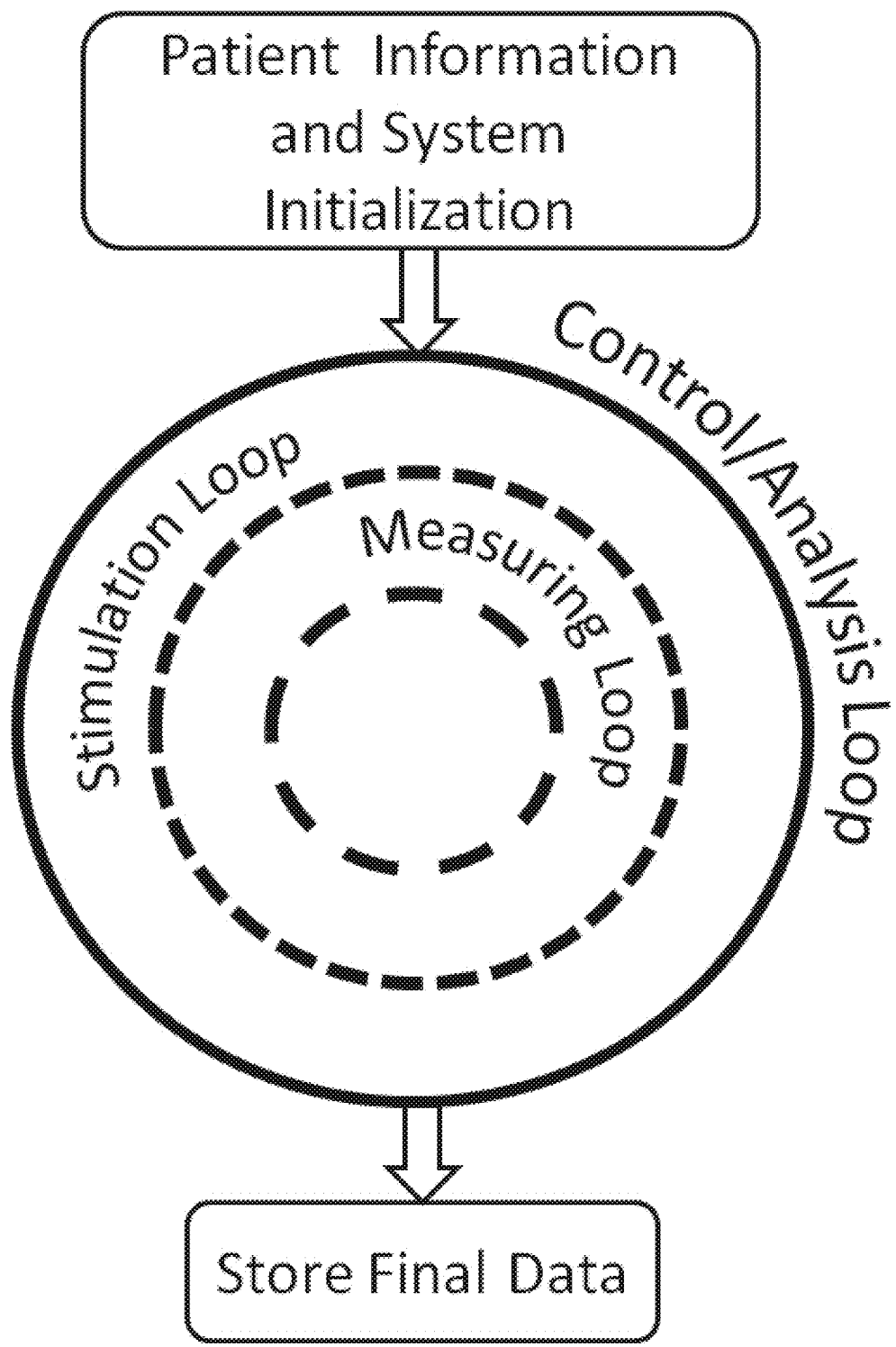
FIG. 12 is a flow chart illustrating process loops according to another non-limiting embodiment of the present invention.

As FIG. 12 illustrates, the outer-most loop is the control/analysis loop, the middle loop is the stimulation loop, and the inner-most loop is the monitoring loop. The control/analysis loop controls the microprocessor 1000 of the graphical user interface 508 and calls the inner loops directly or indirectly to initialize and coordinate the actions of the neuro-selective stimulator 502 and the cortical activity monitor 504, to gather data generated by those components, and to deactivate those components after the desired data is obtained. The control/analysis loop also analyzes that data in real time as it is being generated by the neuro-selective stimulator 502 and the cortical activity monitor 504 and instructs the display device 1006 to display portions of that data as it is generated and analyzed.

The following sequence list describes an exemplary control/analysis loop process performed by the graphical user interface 508:

1. Initialize (boot) the algometer's 500 components 502-508, perform internal system diagnostics, log/report system status, and initiate user graphical user interface 508 (unless system errors indicate a device malfunction requiring attention);
2. Initialize graphical user interface 508 for receiving user input via the input device 1004 for selecting the desired function and setting patient-specific parameters;
3. Provide instructions to user for placing electrodes 510, NIRS sensors 514, and/or EEG electrodes 1100 based on input received via the input device 1004;
4. Provide power to the neuro-selective stimulator 502, the cortical activity monitor 504, and component interface 506 via the power bus 906 and instruct the microprocessor 900 of the component interface 506 to place them in ready and wait mode:
   a. Initialize low-voltage circuit 600 and high voltage circuit 602 of the neuro-selective stimulator 502,
   b. Initialize current driver circuits 700 and 702, photodetector circuits 704 and 706, multiplexor 708, and ADC 710 of cortical activity monitor 504, and
   c. Initialize timers in microprocessor 900, memory 902, and PIA 904 of the component interface 506;
5. Select algorithm based on user input and use it to select cycle time and neuro-specific frequency and intensity of electrical stimulation and to select parameters of oximetry based on user input;
6. Receive instructions from user to begin applying neuro-specific electrical stimulation with the electrodes 510 and monitoring hemodynamic and/or neurophysiological responses with the NIRS sensors 514 and/or EEG electrodes 1100;
7. Instruct the microprocessor 900 of the component interface 506 to begin monitoring hemodynamic and/or neurophysiological changes with the cortical activity monitor 504:
   a. Initiate measuring loop to collect baseline measurement of cortical activity without neuro-specific electrical stimulation being applied (see discussion of monitoring loop provided below), and
   b. Send the data collected by the microprocessor 900 of the component interface 506 (NIRS and/or EEG data only) to the microprocessor 1000 of the graphical user interface 508 for further processing in the analysis/control loop;
8. Quantify collected data and store as a baseline value for the patient in the memory 1002;
9. Instruct the microprocessor 900 of the component interface 506 to begin applying neuro-specific electrical stimulation to the patient with the neuro-selective stimulator 502:
   a. Initiate stimulation loop to apply electrical stimulation with a neuro-specific frequency and intensity for a predetermined cycle time (see discussion of stimulation loop provided below),
   b. Start timing length of time electrical stimulation is applied with clock timer at the microprocessor 1000 of the graphical user interface 508,
   c. If the data received by the microprocessor 900 at the component interface 506 indicates that the neuro-specific electrical stimulation is being applied with an intensity above a sub-noxious level, instruct the microprocessor 900 of the component interface 506 to stop applying neuro-specific electrical stimulation to the patient with the neuro-selective stimulator 502, else instruct the microprocessor 900 of the component interface 506 to stop applying neuro-specific electrical stimulation to the patient with the neuro-selective stimulator 502 after the clocking timer indicates that a predetermine amount of time has elapsed since the electrical stimulation began,
   d. Start timing length of time electrical stimulation is NOT applied with clock timer at the microprocessor 1000 of the graphical user interface 508,
   e. After a predetermine amount of time has passed since the electrical stimulation stopped, repeat steps a-d for a predetermined number of stimulation cycles before instructing the microprocessor 900 of the component interface 506 to stop applying neuro-specific electrical stimulation to the patient with the neuro-selective stimulator 502, and f. Send the data collected by the microprocessor 900 of the component interface 506 (NIRS and/or EEG data plus stimulation data) to the microprocessor 1000 of the graphical user interface 508 for further processing in the analysis/control loop, and 10. Quantify collected data, compare to baseline value, and store as a neuro-specific hemodynamic and/or neurophysiological response for the patient in the memory 1002 of the graphical user interface 508;

11. If comparison determines that the value of the neuro-specific response is more than a predetermined amount greater than the baseline value, instruct the microprocessor 900 of the component interface 506 to repeat steps 9 and 10 a predetermined number of times using the same neuro-specific frequency and intensity, else instruct the microprocessor 900 of the component interface 506 to repeat steps 9 and 10 using electrical stimulation with a greater neuro-specific intensity;

12. Convert the quantified value of the NIRS and/or EEG data into a meaningful measure of the patient's pain-related cortical activity;

13. Instruct the microprocessor 900 of the component interface 506 to stop monitoring hemodynamic and/or neurophysiological changes with the cortical activity monitor 504;

14. Store quantified value as an objective pain measurement for patient in the memory 1002 of the graphical user interface 508;

15. Generate dynamic display of results on display device 1006.

Figure 13:
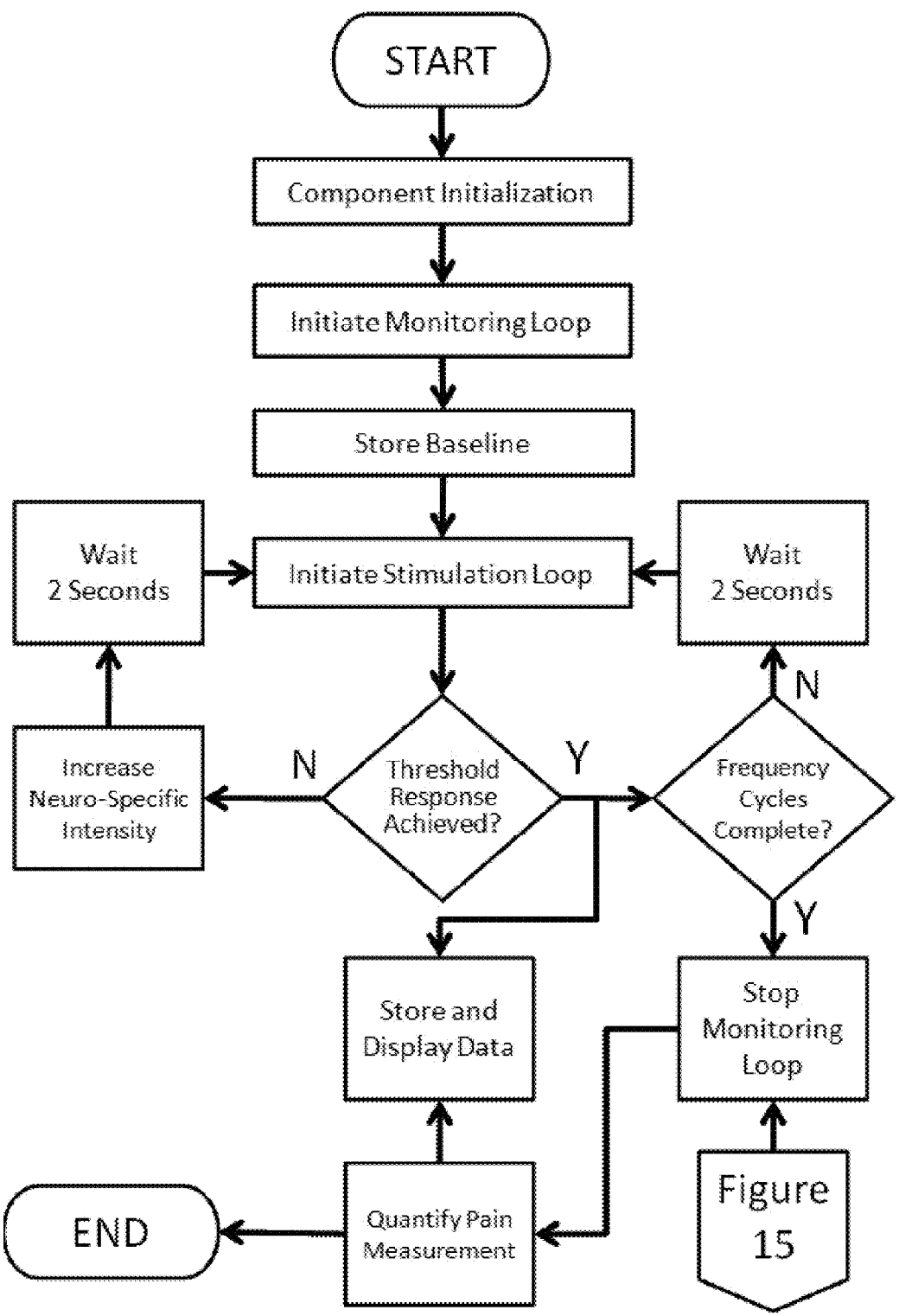
FIG. 13 is a flow chart illustrating a control/analysis loop process according to another non-limiting embodiment of the present invention.

FIG. 13 is a flow chart illustrating the steps of that exemplary process.

As set forth in those steps and FIG. 13, the control/analysis loop initiates the measuring loop and uses the cortical activity monitor 504 to establish a baseline amount cortical activity based on hemodynamic and/or neurophysiological changes occurring in a patient's cortical regions when no neuro-specific electrical stimulation is being applied with the neuro-selective stimulator 502. After that baseline is established, control/analysis initiates the stimulation loop and uses the neuro-selective stimulator 502 apply neuro-specific electrical stimulation to the patient while the cortical activity monitor 504 continues monitoring the hemodynamic and/or neurophysiological changes occurring in the patient's cortical regions. The neuro-specific electrical stimulation is applied in on-off cycles (i.e., a period of simulation being applied followed a period of stimulation NOT being applied) that are repeated a predetermined number of times (e.g., 50) at a neuro-specific frequency and intensity (e.g., 2000 Hz and 2.2 mA). The length of those on-off stimulation cycles will vary according to the patient-specific variables input with the input device 1004 (e.g., location of stimulus, medical or physical condition of patient, etc.) but will typically last a few seconds and will always incorporate an "off" period and an "on" period in each cycle. That series of on-off stimulation cycles is hereinafter referred to as a "frequency cycle" because they are all applied at the same neuro-specific frequency according to the nerve fiber being targeted (e.g., 5 Hz for C fibers, 250 Hz for Aδ fibers, and 2000 Hz for Aβ fibers).

After data has been gathered for a frequency cycle, the control/analysis loop analyzes that data with the microprocessor 1000 of the graphical user interface 508 to determine whether a threshold level of sub-noxious stimulation has been experienced by the patient. If the threshold level of sub-noxious stimulation is experienced, the stimulation loop will repeat the frequency cycle a predetermined number of times. Otherwise, the microprocessor 1000 of the graphical user interface 508 will instruct the microprocessor 900 of the component interface 506 to increase the intensity of the neuro-specific electrical stimulation being applied with the neuro-selective stimulator 502 and perform a frequency cycle at that new intensity (e.g., 2000 Hz and 2.3 mA). The intensity will be increased incrementally until the threshold level of sub-noxious stimulation is experienced, at which point the stimulation loop will repeat the frequency cycle at that neuro-specific frequency and intensity a predetermined number of times.

The control/analysis loop continuously gathers data with the cortical activity monitor 504 during each frequency cycle and analyzes it to provide an objective measure of pain experienced by the patient to whom the neuro-specific electrical stimulation was applied. More specifically, the microprocessor 1000 of the graphical user interface 508 quantifies the value of the NIRS data (i.e., the differential infrared absorption data reflecting neuro-specific changes in hemodynamic response parameters) and/or EEG data (i.e., the differential electrical activity data representing neuro-specific changes in biopotential response parameters) measured by the cortical activity monitor 504 into a meaningful measure of the patient's pain-related cortical activity (e.g., a pain score, an SDT, etc.). For example, an average measured change in total hemoglobin (HbT) of 5.2 μmol/L during a frequency cycle could be correlated to an SDT value of 8 on a scale of 1 to 12. A similar correlation can be performed using Fisher's Z values when EEG is used in combination with or in place of NIRS. That objective pain measurement is then stored for that patient on the memory 1002 of the graphical user interface 508.

A similar process can be implemented with the algometer 500 of the present invention using noxious stimulation (e.g., surgery, venipuncture, arterial puncture, heel-lance, intravenous cannulation, endotracheal tube introduction, endotracheal tube suctioning, gavage insertion for feeding, removal of electrode leads and tape, etc.) manually applied by a user in a clinical setting. In that instance, the stimulation loop will be omitted or utilized prior to that manually applied noxious stimulation. For example, a user can select a function with the input device 1004 of the graphical user interface 508 in which the exemplary process described above will be used to determine the SDT and then repeated without applying neuro-specific electrical stimulation to determine a pain score based on the cortical activity measured in response to the manually applied noxious stimulation. In that example, the user would receive instructions on the appropriate time(s) to manually apply the noxious stimulation via the display device 1006 so as to coordinate the noxious stimulation with the time that the cortical activity monitor 504 will measure the patient's cortical activity. And the microprocessor 1000 of the graphical user interface will quantify that cortical activity with a pain score, using the patient's previously determined SDT as a reference measurement. The patient's cortical activity with no stimulation being applied will serve as the baseline for both the SDT and the pain score. In that manner, baseline and SDT values can be determined in patients before clinical interventions and serve as valuable comparators for calculating pain scores after manually applied noxious stimulation.

Those baseline and SDT values may also be used to determine the effects of analgesics and other pain interventions. In that instance, the exemplary process described above will be repeated over time in a patient who is receiving an intervention intended to treat pain and used to determine that patient's SDT at different points during that treatment. The microprocessor 1000 of the graphical user interface 508 will store those SDT values with the corresponding dosage information on the memory 1002 of the graphical user interface 508 and compare those values over time to identify the onset of tolerance to the intervention or the onset of analgesic-induced toxicity in the patient. For example, the onset of tolerance to analgesics will be identified when there is a trend of increased analgesic dosage amounts over time while maintaining the same SDT. And the onset of hyperalgesia will be identified when there is a trend of decreased SDTs over time while maintaining the same analgesic dosage amounts.

ii. Stimulation Loop

The stimulation loop controls the microprocessor 900 of the component interface 506 and the neuro-selective stimulator 502 and provides electrical stimulation at frequencies that selectively stimulate specific sensory nerve fibers (e.g., C, Aδ, and Aβ fibers) so as to elicit specific activity in a patient's cortical regions—in particular, those associated with the patient's somatosensory system. The microprocessor 900 of the component interface 506 and the low-voltage circuit 600 and high voltage circuit 602 of the neuro-selective stimulator 502 are initialized at step 4 of the control/analysis loop. And the following sequence list describes an exemplary stimulation loop process performed by the microprocessor 900 of the component interface 506 and the neuro-selective stimulator 502 at step 9 of the control/analysis loop:

1. Receive instructions from the microprocessor 1000 of the graphical user interface 508 to begin applying electrical stimulation at a neuro-specific frequency and intensity;
2. Configure sine wave generator 604 to begin producing continuous sine wave signals at neuro-specific frequency selected at step 5 of the control/analysis loop;
3. Configure digital potentiometer 606 to begin applying an initial voltage output of zero to the sine wave signals;
4. Select "on" and "off" times of neuro-specific electrical stimulation according to the cycle time selected at step 5;
5. Start timing length of time voltage output of digital potentiometer 606 is zero with clock timer at the microprocessor 900 of the component interface 506;
6. Configure digital potentiometer 606 to begin applying a voltage output to the sine wave signals that corresponds to the neuro-specific intensity selected at step 5 of the control/analysis loop after the selected "off" time has elapsed;
7. Start timing length of time voltage output of digital potentiometer 606 is at the neuro-specific intensity with clock timer at the microprocessor 900 of the component interface 506;
8. Configure digital potentiometer 606 to begin applying a voltage output of zero to the sine wave signals after the selected "on" time has elapsed;
9. Repeat steps 5-8 for a predetermined number of on-off stimulation cycles;
10. Notify microprocessor 1000 of the graphical user interface 508 that on-off stimulation cycles are completed and wait for further instruction;
11. If comparison at step 10 of control/analysis loop determines that the value of the neuro-specific response is more than a predetermined amount greater than the baseline value, receive instructions from the microprocessor 1000 of the graphical user interface 508 to repeat steps 6-9 a predetermined number of times using the same neuro-specific frequency and intensity, else receive instructions from the microprocessor 1000 of the graphical user interface 508 to repeat steps 6-9 using electrical stimulation with a greater neuro-specific intensity.

Figure 14:
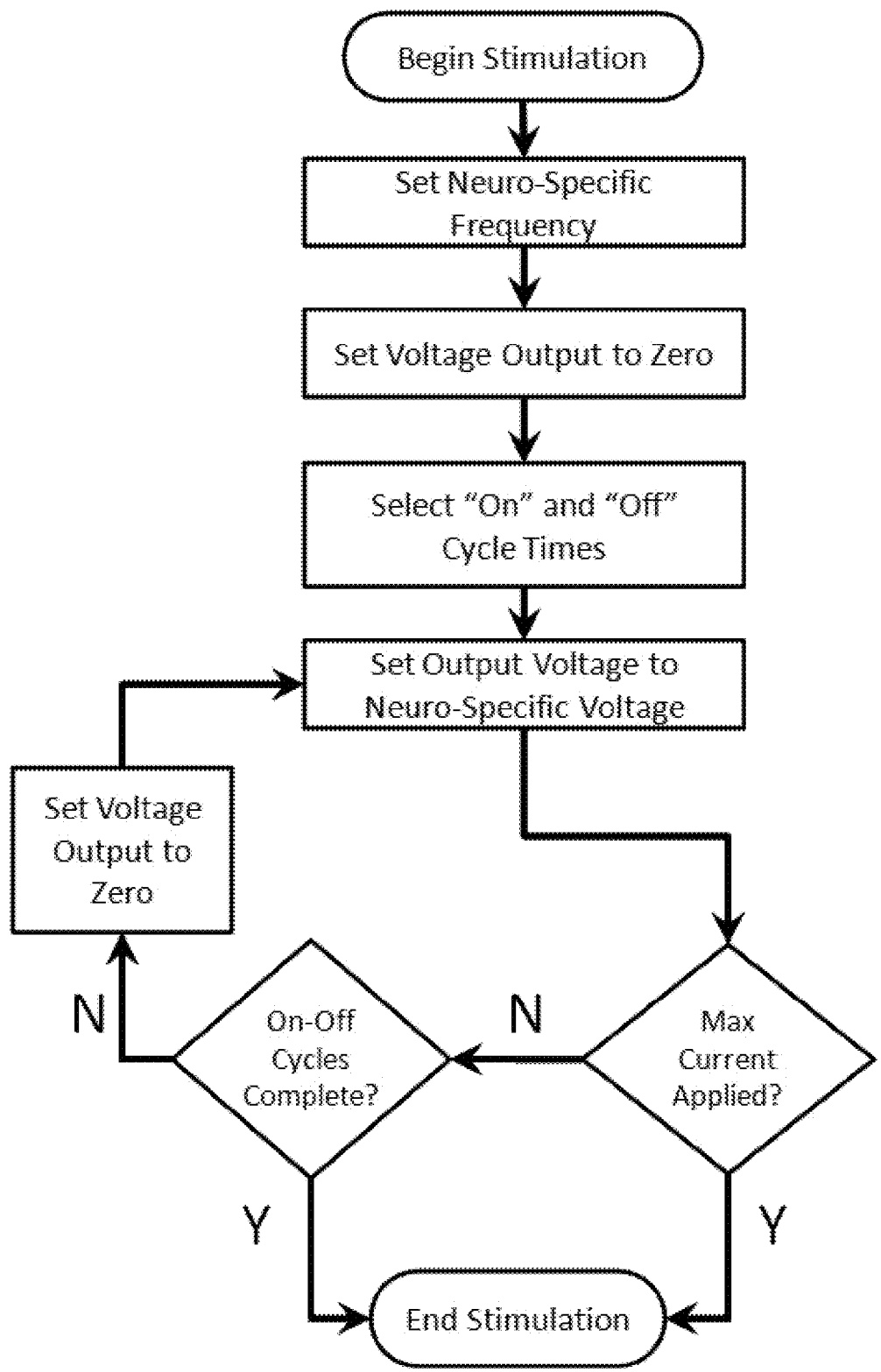
FIG. 14 is a flow chart illustrating a stimulation loop process according to another non-limiting embodiment of the present invention.

FIG. 14 is a flow chart illustrating the steps of that exemplary process.

As set forth in those steps and FIG. 14, the microprocessor 1000 of the graphical user interface 508 sends instructions to the microprocessor 900 of the component interface 506 to begin applying electrical stimulation at a neuro-specific frequency and intensity. Based on those instructions, the microprocessor 900 of the component interface 506 instructs the sine wave generator 604 to begin producing continuous sine wave signals at that frequency and instructs the digital potentiometer 606 to begin applying a voltage to those signals. The initial voltage is zero, but that voltage is ramped up to a voltage that corresponds to a neuro-specific intensity. As discussed above, that neuro-specific voltage is converted to a neuro-specific current by the high-voltage circuit 602 of the neuro-selective stimulator 502.

Based on the on-off cycle times selected by the microprocessor 1000 of the graphical user interface 508, neuro-selective stimulator 502 cycles between "on" and "off" periods or neuro-specific electrical stimulation until a predetermined number of on-off cycles (e.g., 50) are completed. At that point, the stimulation loop will stop until reinitiated by the control/analysis loop which, as discussed above, may include selecting an incrementally larger current intensity with which to generate the neuro-specific electrical stimulation. And as also discussed above the control/analysis loop will stop and reinitiate the stimulation loop a predetermined number of times until the desired number of frequency cycles are completed. The stimulation loop will also stop if the current applied via the electrodes 510 is detected as being higher than a predetermined value, such as a current with an intensity large enough to achieve the targeted nerve fiber's threshold action potential but small enough that the patient does not consciously perceive a feeling of pain (i.e., >sub-noxious stimulation).

The cycle times, number cycle sequences, minimum and maximum current intensities, and degrees of increase in current intensities are determined by the algorithm selected by the microprocessor 1000 of the graphical user interface 508 based on the user input received via the input device 1004. The number of frequency cycles is selected to provide a sufficient number of data points to provide statistical accuracy when quantifying the pain perceived by the patient. And if the maximum current intensity is reached without the minimum threshold response to stimulation being observed, that maximum current intensity will be stored in the memory 1002 of the graphical user interface 508 as the threshold amount. Thus, if an SDT is being determined with the algometer 500, that value will be used to calculate the patient's SDT.

iii. Monitoring Loop

Figure 15:
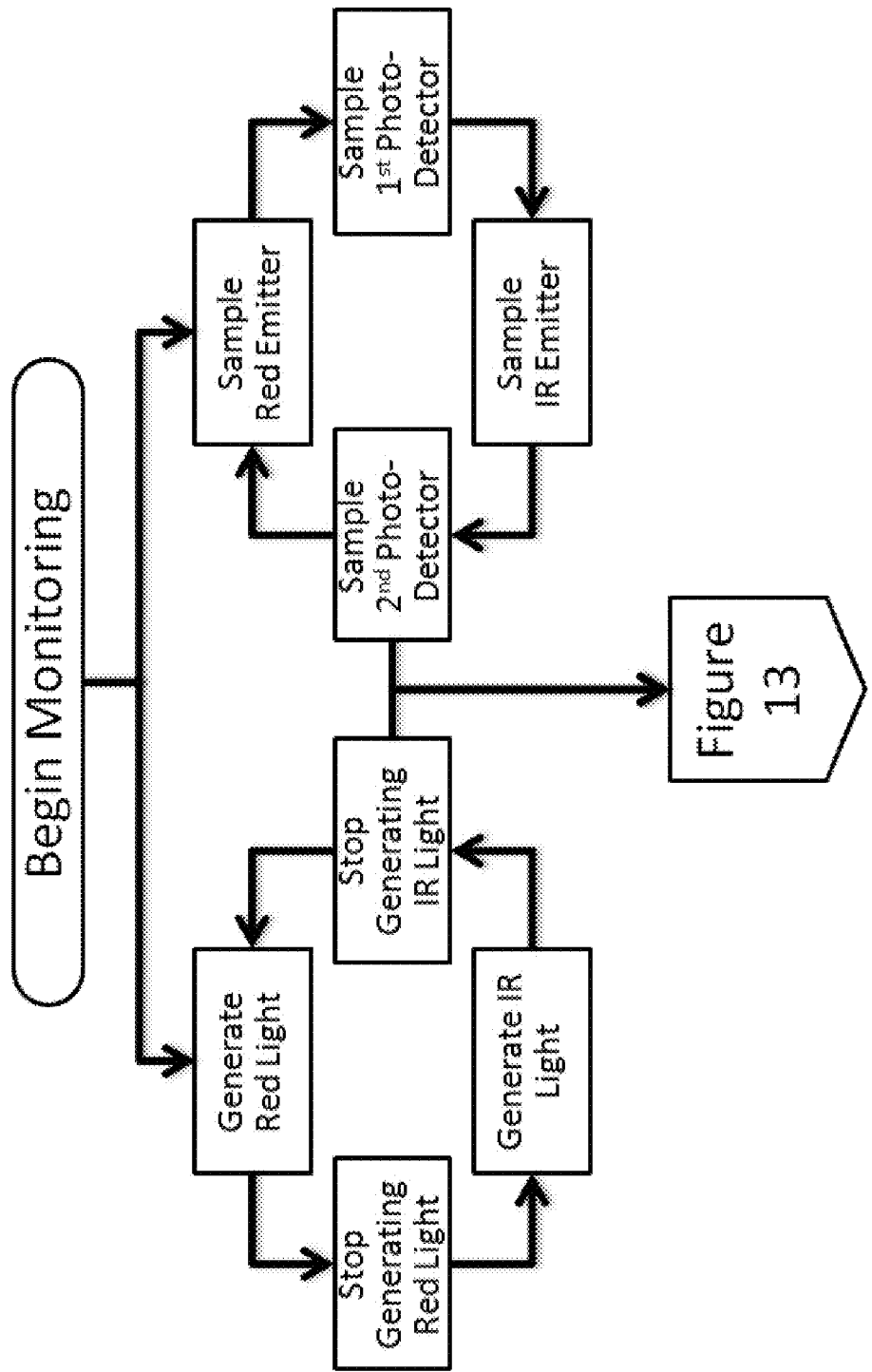
FIG. 15 is a flow chart illustrating a monitoring loop process according to another non-limiting embodiment of the present invention.

The monitoring loop controls the microprocessor 900 of the component interface 506 and the cortical activity monitor 504 and provides an objective measurement of pain based on hemodynamic and/or neurophysiological changes in the cortical regions of a patient's brain in response to the sub-noxious, neuro-specific electrical stimulation applied with the neuro-selective stimulator 502 and/or manually applied noxious stimulation. The microprocessor 900 of the component interface 506 and the subcomponents 700-710 of the cortical activity monitor 504 are initialized at step 4 of the control/analysis loop. And the following sequence list describes an exemplary monitoring loop process performed by the microprocessor 900 of the component interface 506 and the neuro-selective stimulator 502 at steps 7-13 of the control/analysis loop:

1. Initialize first clock timer at the microprocessor 900 of the component interface 506 for generating control signals to alternately select which of the red and IR light emitters 714 and 718 will receive an excitation current;

2. Alternately generate requisite current excitation level for the red and IR light emitters 714 and 718 within current driver circuits 700 and 702 based on the control signals from the first timer;

3. Initialize second clock timer at the microprocessor 900 of the component interface 506 for generating control signals to alternately select which channel of the multiplexer 708 to be processed by the ADC 710;

4. Alternately sample and convert signals from first current driver circuit 700, second current driver circuit 702, first photo-detector circuit 704, and second photo-detector circuit 706 with the ADC 710 based on the channel of the multiplexer selected with the control signals from the second timer;

FIG. 15 is a flow chart illustrating the steps of that exemplary process.

As set forth in those steps and FIG. 15, the microprocessor 1000 of the graphical user interface 508 sends instructions to the microprocessor 900 of the component interface 506 to begin alternately generating red and IR light with the red and IR light emitters 714 and 718 of the first and second current driver circuits 700 and 702. The microprocessor 1000 of the graphical user interface 508 also sends instructions to the microprocessor 900 of the component interface 506 to begin alternately sampling the signals generated at the first current driver circuit 700, second current driver circuit 702, first photo-detector circuit 704, and second photo-detector circuit 706 as the red and IR light emitters 714 and 718 emit red and IR light and the first and second photo-detectors 720 and 728 receive the reflected portions of that light. Those two alternating cycles are performed continuously until the microprocessor 1000 of the graphical user interface 508 sends instructions to the microprocessor 900 of the component interface 506 to stop the monitoring loop.

The first timer preferably generates 25% duty cycle pulses at 125 Hz frequency to enable/disable the activation of the red and IR emitters 714 and 718. The second timer preferably has a 0.5 ms period at which time a new channel of the multiplexer 708 is selected by the for analog-to-digital conversion by the ADC 710. And each cycle of light emission preferably lasts 2 ms such that the four channels of the multiplexer are interleaved to provide signals to the ADC 710 in increments of 0.5 ms. In that configuration, the microprocessor 900 of the component interface 506 gathers fifty data-points during each interleaved 0.5 ms sample, averages them, and sends sixteen sets of those averaged data points to the microprocessor of the graphical user interface 508 every 8 ms for further processing. Each of those average data points includes values of input currents to the red and IR light emitters 714 and 718 and values of currents detected at the first and second photo-detector diodes 720 and 728.

E. Human Algometry

In practice, the algometer of the present invention can be used to (1) objectively quantify pain and the response to noxious and sub-noxious stimuli, (2) determine SDTs and/or pain scores in response to such stimuli and other clinically relevant stimuli, (3) monitor the analgesic effects of drugs and other pain interventions and the efficacy and dose-response relationships of newly developed and/or investigational drugs targeted for the management of pain, (4) determine the onset of tolerance to analgesic and other interventions, and (5) provide a diagnostic characterization of pain, all of which guide the overall management of pain in a patient. Each of those forms of human algometry is discussed separately below.

i. Objective Quantification of Pain

The cortical activity monitoring functionality of the present invention allows the emotional component of pain to be separated from the actual, nociceptive component of pain. The emotional component of pain is removed by using the neuro-selective stimulator 502 to generate action potentials at specific nerve fibers without the patient perceiving nociception (i.e., sub-noxious electrical stimulation). Although the resulting innervations of those nerve fibers is not perceived by the patient, the cortical activity monitor 504 of the present invention is able to measure hemodynamic and/or neurophysiological changes in the cortical regions of the patient's brain in response to that stimuli. Because those measurements are able to separate the nociceptive component of pain from the emotional component of pain and do not require subjective verbal quantifications and/or subjective physician observations, they provide an objective measure of the patient's response to the sub-noxious electrical stimulation.

The emotional component of pain can be further removed from that measurement by monitoring cortical activity at the specific cortical region of the brain associated with nociceptive pain (i.e., the primary somatosensory cortex) and the specific cortical region of the brain associated with emotional pain (i.e., the dorsolateral prefrontal cortex). The hemodynamic and/or neurophysiological changes at those two regions are then correlated with one another to determine the relationship between the emotional component and the nociceptive component. Thus, if a patient is actually perceiving pain, either as a result of the noxious stimulation being manually applied and/or the patient's physical condition, the emotional component can be factored out of the nociceptive component to provide a more accurate, and more objective, measure of the patient's actual, nociceptive pain.

ii. Determining SDTs and Pain Scores

The present invention uses a testing paradigm that differs from conventional apparatus/methods, such as PPT and PTT, in that the determination of SDTs and pain scores utilizing neuro-specific electrical stimulation of self-limiting duration for which the intensity is controlled based on objective measurements of hemodynamic and/or neurophysiological changes measured with the cortical activity monitor 504. A compilation of hemodynamic and/or neurophysiological responses to commonly encountered, clinically relevant painful or noxious stimuli along with control (e.g., no stimulation) or other reference responses are used to create a pain scale against which SDTs and/or pain scores can be evaluated and reported. That testing paradigm also allows for the inclusion of manually applied noxious stimulation, which can be separated from its emotional component to provide an objective measurement of nociceptive pain, as discussed above. SDT values and pain scores can be assigned to a patient at specific frequencies and intensities of electrical stimulation using a look-up table, or scale, stored on the memory 1002 of the graphical user interface 508 to identify an SDT value or pain score associated with the measured amount of hemodynamic and/or neurophysiological change for that patient at those frequencies and intensities of electrical stimulation. Different look-up tables are provided for different patients based on known physiological differences between those patients so as to form a library of reference responses that can be used to determine pain scores and/or SDTs for patients.

Figure 16:
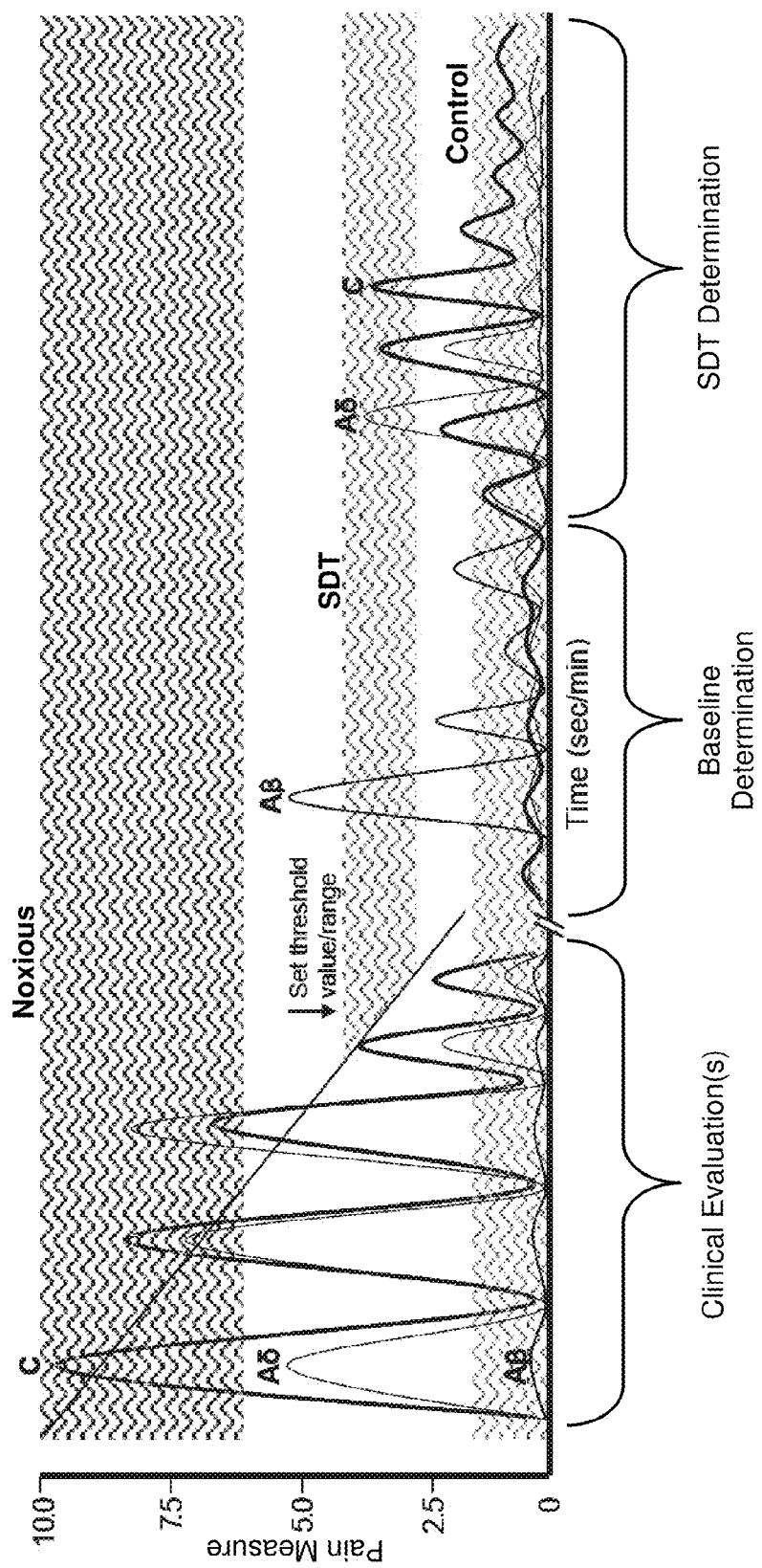
FIG. 16 is a graph that illustrates pain measurements plotted over time during a pain assessment process performed according to a non-limiting embodiment of the present invention.

As FIG. 16 illustrates, those look-up tables are defined via clinical evaluations (e.g., clinical trials, patient encounters, etc.). More specifically, the cortical activity monitor 504 is used to measure hemodynamic and/or neurophysiological changes in the cortical regions of a plurality of different patient's brain as a plurality of different levels of stimulation are applied to the patient. That stimulation includes noxious stimulation, and it may be applied either with the neuro-selective stimulator 502 with conventional thermal, chemical, or mechanical stimuli. Because the neuro-selective stimulator 502 will generally not be used to apply anything other than sub-noxious stimulation, it will have a separate "clinical trial" mode that is configured to allow it to be used to apply noxious stimulation during clinical trials. That mode will also be configured to receive input via the input device 1004 of the graphical user interface for quantifying the pain experienced by the patient. Those quantifications will be matched with the measured level of hemodynamic and/or neurophysiological changes measured with the cortical activity monitor 504 to identify a range of SDT values for different patients with different physiological characteristics (e.g., patients of different age, weight, medical condition, medical history, etc.).

The ranges of SDT values determined for different patients are used to create the look-up tables. And the ranges in those loop-up tables are used to identify SDTs for subsequently evaluated patients by matching the measured levels of hemodynamic and/or neurophysiological changes for those subsequently evaluated patients to values in the loop-up tables that correspond to the SDTs obtained for previously evaluated patients with similar physiological characteristics to the subsequently evaluated patients. As FIG. 16 illustrates, and as discussed above with respect to the control/analysis loop of the algometer software, the process of subsequently evaluating patients using those loop-up tables includes measuring a baseline level of hemodynamic and/or neurophysiological changes in the patient without any stimulation being applied to use as a control. Neuro-specific electrical stimulation is then applied with the neuro-selective stimulator 502 until hemodynamic and/or neurophysiological changes are measured with the cortical activity monitor 504 that fall within the subject SDT range. The corresponding frequency and intensity of the neuro-specific electrical stimulation used to obtain that threshold level of hemodynamic and/or neurophysiological change in the patient is then associated with that patient's SDT and stored on the memory 1002 of the graphical user interface 508 for use in future evaluations of that patient.

Because the evaluations used to define the look-up tables include the application of noxious pain, they are preferably performed during clinical evaluations specifically designed to establish SDT ranges for different patients with different physiological characteristics. The algometer 500 is then preprogrammed with the appropriate look-up tables before being used in other clinical settings. Accordingly, the algometer 500 can be utilized in those other clinical settings to apply sub-noxious stimulation only. Look-up tables for pain scores can be defined and used in substantially the same manner.

iii. Monitoring Effects and Efficacy of Drugs and Pain Interventions

The ability of the present invention to monitor hemodynamic and/or neurophysiological changes in response to neuro-specific electrical stimulation allows the present invention to determine the analgesic effects drugs and other pain interventions as well as the efficacy and dose-response relationships of newly developed and/or investigational drugs targeted for the management of pain. More specifically, different analgesic drug classes modulate different nerve fibers. And by targeting those specific fibers with neuro-specific electrical stimulation, the present invention is able to evaluate the effect of the specific drug that modulates those nerve fibers.

For example, opioids modulate C fibers but not Aβ fibers. Accordingly, neuro-specific electrical stimulation can be applied to C fibers at a frequency of 5 Hz to measure the effect of an opioid. And by utilizing that neuro-specific electrical stimulation in conjunction with the objective measurements provided by the cortical activity monitor 504 of the present invention, the effects of analgesic drugs and other pain interventions can be measured in specific sensory nerve fibers. Thus, the present invention can be used with a quantitative sensory testing (QST) paradigm to objectively measure pain responses to specific pain interventions.

Figure 17:
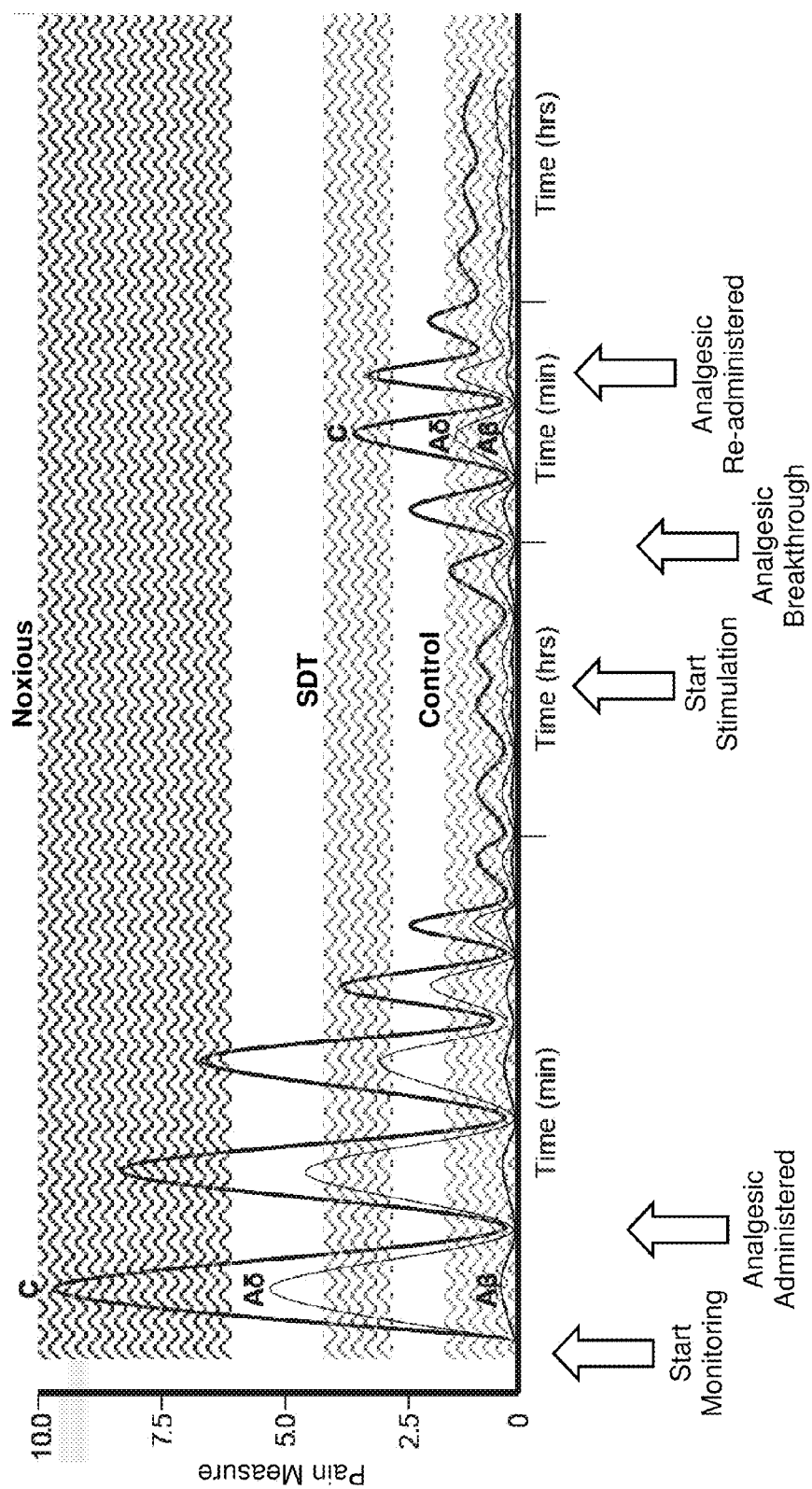
FIG. 17 is a graph that illustrates pain measurements plotted over time during another pain assessment process performed according to another non-limiting embodiment of the present invention.

As FIG. 17 illustrates, the SDT values provided in the look-up tables described above can be used as part of testing the effect of a specific pain intervention. In that figure, the cortical activity monitor 504 is used to begin measuring the pain a patient is experiencing before a pain intervention is administered, such as immediately after a patient has undergone a surgical procedure. At that point, no electrical stimulation is applied with the neuro-selective stimulator 502. The pain intervention is then administered, and the hemodynamic and/or neurophysiological changes in the cortical regions of the patient's brain are measured until they drop below the patient's SDT. That drop in measurements indicates that the pain intervention was effective.

After the hemodynamic and/or neurophysiological changes are below the patient's SDT for a predetermined amount of time, neuro-specific electrical stimulation is applied to the patient with the neuro-selective stimulator 502 using a frequency specific to the nerve fiber modulated by the subject pain intervention (e.g., 5 Hz for an opioid). The electrodes 510 are placed on an extremity that is not the source of the patient's pain (e.g., finger, toe, etc.) so as to measure the systemic effect of the analgesic on a particular nerve fiber type rather than on the source of the patient's pain. And the current is maintained at an intensity within the SDT range determined for the patient so that hemodynamic and/or neurophysiological changes below that threshold value will indicate that, that the pain intervention is acting effectively and hemodynamic and/or neurophysiological changes at or above that threshold value will indicate that the pain intervention is wearing off.

In response to such an indication, the algometer 500 can generate an alert, such as displaying a warning on the display device 1006 of the graphical user interface, it can communicate with a drug-dispensing system to cause that system to automatically re-administer the pain intervention in the appropriate amount, and/or it can communicate with a hospital's central monitoring system to generate an alert at some other location, such as a nurses station. As a result of those alerts or that communication with the drug-dispensing system, the pain intervention will be re-administered to the patient. The algometer 500 will continue to monitor the patient's pain and re-administer the pain intervention in that way as required to ensure the patient's pain remains below a noxious level.

iv. Determining the Onset of Tolerance

The present invention can determine the onset of tolerance to certain pain interventions by repeating the processes illustrated in FIGS. 16 and 17 over an extending period of time. The process illustrated in FIG. 16 is intermittently repeated within a specific dosing to identify changes in the patient's SDT, and the process of FIG. 17 is continuously repeated to determine the effectiveness of the pain intervention in response to that dosing. The patient's SDT can then be adjusted over time so that the point where the pain intervention is wearing off can be more accurately identified. And when a decrease in the patient's SDTs is exhibited over time in response to similar intensities of neuro-specific electrical stimulation, the onset of tolerance will be identified. The algometer 500 can generate alerts or adjust dosing when it identifies the onset of tolerance in a similar manner to that described above when a pain intervention needs to be re-administered.

v. Diagnostic Characterization of Pain

The ability of the present invention to monitor hemodynamic and/or neurophysiological changes in response to neuro-specific electrical stimulation also allows the present invention to make a diagnostic characterization of pain in various pain conditions. More specifically, different pain conditions modulate different nerve fibers. And by targeting those specific fibers with neuro-specific electrical stimulation, the present invention is able to diagnose the pain condition the patient is experiencing.

For example, because neuropathic pain is modulated via Aβ fibers. Accordingly, neuro-specific electrical stimulation can be applied to Aβ fibers at a frequency of 2000 Hz to detect the presence of neuropathic pain over an injury. In that instance, the electrodes 510 will be placed over the area on the patient's body that is the source of the pain. And a measurement of noxious or near-noxious levels of pain in response to sub-noxious neuro-specific stimulation of Aβ fibers—sensory fibers generally not associated with nociceptive pain—at the source of the patient's pain will indicate that the patient is suffering neuropathic pain. Similar techniques can be used to diagnose other pain conditions (e.g., hyperalgesia, allodynia, etc.).

F. Supplemental Disclosure

In addition to the foregoing disclosure, the disclosures of following articles are hereby incorporated by in there entirety as if fully set forth herein:

1. American Medical Association, "Module 6: Pediatric Pain Management", *Pain Management Series*, http://www.ama-cmeonline.com/pain_mgmt/module06/index.htm (February 2010);
2. Angst, M. S., D. R. Drover, et al., "Pharmacodynamics of orally administered sustained-release hydromorphone in humans", *Anesthesiology*, vol. 94(1), 63-73 (2001);
3. Bartocci, M., L. L. Bergqvist, et al., "Pain activates cortical areas in the preterm newborn brain", *Pain*, 122(1-2), 109-117 (2006);
4. Becerra, L. et al. "Diffuse Optical Tomography Activation in the Somatosensory Cortex: Specific Activation by Painful vs. Non-Painful Thermal Stimuli", *PLoS ONE*, vol. 4(11), 1-5 (2009);
5. Becerra, L. et al. "Diffuse Optical Tomography of Pain and Tactile Stimulation: Activation in Cortical Sensory and Emotional Systems", *Neuroimage*, vol. 41(2), 252-259 (2008);
6. Bornhövd, K., M. Quante, et al., "Painful stimuli evoke different stimulus-response functions in the amygdala, prefrontal, insula and somatosensory cortex: a single-trial fMRI study", *Brain*, vol. 125(6), 1326-1336 (2002);
7. Brennum, J., J. B. Dahl, et al., "Quantitative sensory examination of epidural anaesthesia and analgesia in man: effects of pre- and post-traumatic morphine on hyperalgesia", *Pain*, vol. 59(2), 261-271 (1994);
8. Carbajal, R. et al., "Epidemiology and Treatment of Painful Procedures in Neonates in Intensive Care Units", *JAMA*, vol. 300(1), 60-70 (2008);
9. De Pascalis, V. and Cacace, I., "Pain perception, obstructive imagery and phase-ordered gamma oscillations", *Int. J. Psychophysiology*, vol. 56(2), 157-169 (2005);
10. Finkel, J. C., V. G. Besch, et al., "Effects of aging on current vocalization threshold in mice measured by a novel nociception assay", *Anesthesiology*, vol. 105(2), 360-369 (2006);
11. Finkel, J. C., C. I. Yang, et al., "Neuro-selective sensory electrodiagnostic evaluation of 4% liposomal topical lidocaine", *Anesth Analg*, vol. 94(5), 1259-1262, Table of Contents (2002);
12. Gustorff, B., K. H. Hoerauf, et al., "Comparison of different quantitative sensory testing methods during remifentanil infusion in volunteers", *Br J Anaesth*, vol. 91(2), 203-208 (2003);
13. Hoshi, Y. and Tamura, M., ""Dynamic multichannel near-infrared optical imaging of human brain activity", *American Physiological Society*, 1842-1846 (1993);
14. Kalinowski, M. and Wagner, H., "Sedation and pain management in interventional radiology", *Adjunctive Therapy*, 14-18;
15. Katims, J. J., "Electrodiagnostic Functional Sensory Evaluation of the Patient with Pain: A Review of the Neuroselective Current Perception Threshold and Pain Tolerance Threshold", *Pain Digest*, vol. 8, 219-230 (1998);
16. Katims, J. J., "Neuro-selective current perception threshold quantitative sensory test", *Muscle Nerve*, vol. 20(11), 1468-1469 (1997);
17. Katims, J. J., D. M. Long, et al., "Transcutaneous nerve stimulation: Frequency and waveform specificity in humans", *Appl Neurophysiol*, vol. 49(1-2), 86-91 (1986);
18. Kiso, T., Y. Nagakura, et al., "Neurometer measurement of current stimulus threshold in rats", *J Pharmacol Exp Ther*, vol. 297(1), 352-356 (2001);
19. Koga, K., H. Furue, et al., "Selective activation of primary afferent fibers evaluated by sine-wave electrical stimulation", *Mol Pain*, vol. 1(1), 13 (2005);
20. Liu, S., D. J. Kopacz, et al., "Quantitative assessment of differential sensory nerve block after lidocaine spinal anesthesia", *Anesthesiology*, vol. 82(1), 60-63 (1995);
21. Liu, S. S., J. C. Gerancher, et al., "The effects of electrical stimulation at different frequencies on perception and pain in human volunteers: epidural versus intravenous administration of fentanyl", *Anesth Analg*, vol. 82(1), 98-102 (1996);
22. Lotsch, J. and M. S. Angst, "The μ-opioid agonist remifentanil attenuates hyperalgesia evoked by blunt and punctuated stimuli with different potency: a pharmacological evaluation of the freeze lesion in humans", *Pain*, vol 102(1-2), 151-161 (2003);
23. Luginbuhl, M., T. W. Schnider, et al., "Comparison of five experimental pain tests to measure analgesic effects of alfentanil", *Anesthesiology*, vol. 95(1), 22-29 (2001);
24. MacLeon, David B., "Calibration and Validation of the Nonin Non-invasive Regional Oximeter with Cerebral Sensor", Press Release (www.nonin.com).
25. Maltseva, I., et al., "Alpha oscillations as an indicator of dynamic memory operations—anticipation of omitted stimuli", *Int. J. Psychophysiology*, vol. 36(3), 185-197 (2000);
26. McGowan, J. C. and S. K. Wallace, "Synergy of a Combined Near-Infrared Spectroscopy and Blood Oxygenation Level-Dependent Functional Activation Study," *American Journal of Neuroradiology*, 1127-1128 (Aug. 25, 2004);
27. Oda, M., N. Kitagawa, et al., "Quantitative and fiber-selective evaluation of dose-dependent nerve blockade by intrathecal lidocaine in rats", *J Pharmacol Exp Ther*, vol. 312(3), 1132-1137 (2005);
28. Owen-Reece, H., M. Smith, et al., "Near infrared spectroscopy", *Br J Anaesth*, vol. 82(3), 418-426 (1999);
29. Pedersen, J. L. and H. Kehlet, "Secondary hyperalgesia to heat stimuli after burn injury in man," *Pain*, vol. 76(3), 377-384 (1998);
30. Posner, J., A. Telekes, et al., "Effects of an opiate on cold-induced pain and the CNS in healthy volunteers," *Pain*, vol. 23(1), 73-82 (1985);

31. Slater, R., S. Boyd, et al., "Cortical pain responses in the infant brain," *Pain*, vol. 123(3), 332; Author Reply 332-334 (2006);
32. Slater, R., A. Cantarella, et al., "Cortical pain responses in human infants," *J Neurosci*, vol. 26(14), 3662-3666 (2006);
33. Slater, R., M. Fitzgerald, et al., "Can cortical responses following noxious stimulation inform us about pain processing in neonates?," *Semin Perinatol*, vol. 31(5), 298-302 (2007);
34. Tai, K. and Chau, T., "Single-trial classification of NIRS signals during emotional induction tasks: towards a corporeal machine interface", *Journal of NeuroEngineering and Rehabilitation*, col. 6(39), 1-14 (2009);
35. Tay, B., M. S. Wallace, et al., "Quantitative assessment of differential sensory blockade after lumbar epidural lidocaine," *Anesth Analg*, vol. 84(5), 1071-1075 (1997);
36. Tobias, J. D., "Cerebral oxygenation montoring: near-infrared spectroscopy," *Future Drugs*, 235-243 (2006);
37. Wolf, M. and Greisen, G., "Advances in Near-Infrared Spectroscopy to Study the Brain of the Preterm and Term Neonate", *Clin Perinatol*, col. 36, 807-834 (2009);
38. Wray, S., M. Cope, et al., "Characterization of the near infrared absorption spectra of cytochrome aa3 and haemoglobin for the non-invasive monitoring of cerebral oxygenation," *Biochim Biophys Acta*, vol. 933(1), 184-192 (1988); and
39. Yarnitsky, D., E. Sprecher, et al., "Multiple session experimental pain measurement," *Pain*, vol. 67(2-3), 327-333 (1996).

G. Summary

The present invention integrates a neuro-selective stimulator 502 for assessing the physiological integrity of specific sensory pain fiber pathways with a cortical activity monitor 504 for detecting cerebral responses to both sub-noxious and noxious stimuli. The present invention integrates those components using a central microprocessor 900 that automates the delivery of stimuli and the assessment of a patient's response to that stimuli. The neuro-selective stimulator 502 delivers escalating intensities of electrical stimulation at a set of specific frequencies and intensities that can be sensed by specific sensory nerve fibers (i.e., neuro-specific electrical stimulation). The r cortical activity monitor 504 uses NIRS and/or EEG to sample hemodynamic and/or neurophysiological changes in various cortical regions of a patient's brain, including but not limited to the primary somatosensory cortex, the occipital cortex, and the dorsolateral prefrontal cortex, in order to quantify the responses to both sub-noxious and noxious stimuli, either which may automatically be delivered by the neuro-selective stimulator 502 or manually delivered during the conduct of clinical care (e.g. venipuncture, surgical pain, endotracheal tube suctioning, dressing changes, etc.). In turn, the response signals are processed and an SDT and/or pain score are generated.

Placing NIRS probes and/or EEG electrodes 1100 at the various cortical regions of the brain enables the recognition and determination of distinct sensory (e.g., somatosensory cortex), visual (e.g., occipital cortex), and emotional (e.g., dorsolateral prefrontal cortex) responses to various stimuli. Obtaining measurements of NIRS and/or EEG responses from various regions of the brain serves to differentiate the components of the human response to noxious stimuli, such as the nociceptive and emotional components of pain, and provides baseline and/or control measurements to such responses. The processing of those signals ultimately provides for (1) objectively quantifying pain and the response to noxious and sub-noxious stimuli, (2) determining SDTs and/ or pain scores in response to such stimuli and other clinically relevant stimuli, (3) monitoring the effects of analgesic and other interventions intended to treat pain, (4) determining the onset of tolerance to analgesic and other interventions, and (5) providing a diagnostic characterization of pain, all of which guide the overall management of pain in a patient. The resulting algometer 500 is compact with a graphical user interface 508 and display device 1006 that is easily incorporated into a variety of clinical environments and that can be used in combination with or adjunct to other diagnostic modalities.

What is claimed is:

1. A system for objectively measuring pain comprising:
a stimulator configured to apply electrical stimulation of variable intensity to an area of a patient's body;
a monitoring device configured to measure a level of cortical activity at a plurality of different regions of the patient's brain including a primary somatosensory cortex and a dorsolateral prefrontal cortex; and
a microprocessor connected to the stimulator and the monitoring device that is configured to
correlate a first level of cortical activity at the primary somatosensory cortex of the plurality of different regions of the patient's brain with a second level of cortical activity at the dorsolateral prefrontal cortex of the plurality of different regions of the patient's brain to determine the relationship between an emotional component of pain and a nociceptive component of pain and remove the emotional component to derive an activity measurement value, and
correlate the variable intensity of the electrical stimulation with the activity measurement value to determine, based on the correlation, an objective pain representation,
wherein the system further includes:
a pharmacologic-dispensing device that administers pain intervention drugs to the patient in accordance with the determined objective pain representation.

2. The system of claim 1, wherein the stimulator is configured to incrementally increase the intensity of the electrical stimulation until a sensory detection threshold (SDT) level of cortical activity is measured by the monitoring device.

3. The system of claim 1, wherein the stimulator is further configured to apply electrical stimulation to sensory nerve fibers by applying electrical stimulation at a first frequency in order to generate an action potential in Aβ fibers, a second frequency in order to generate an action potential in Aδ fibers, and a third frequency in order to generate an action potential in C fibers.

4. The system of claim 1, wherein the monitoring device utilizes at least one of near infrared spectroscopy (NIRS), electroencephalography (EEG), functional Magnetic Resonance imaging (fMRI), and near infrared imaging (NIRI) to measure the level of cortical activity in the plurality of different regions of the patient's brain.

5. The system of claim 4, wherein the monitoring device utilizes NIRS and a NIRS sensor with emitters and detectors to measure the level of cortical activity in plurality of different regions of the patient's brain.

6. The system of claim 4, wherein the monitoring device utilizes EEG with electrodes as sensors or EEG and NIRS with a combination of electrodes and at least one NIRS sensor as the sensors to measure the level of cortical activity in the plurality of different regions of the patient's brain.

7. The system of claim 1, wherein the microprocessor is further configured to
- accumulate a plurality of measurements of different levels of cortical activity in one or more regions of a plurality of first patients' brains in response to noxious and sub-noxious stimuli with different parameters, the noxious stimuli being applied prior to the sub-noxious stimuli and/or as part of one or more clinical trials;
- correlate the plurality of measurements with a plurality of quantitative values in a pain intensity scale, the quantitative values representing a pain intensity measurement;
- store the plurality of measurements, their corresponding quantitative values, and the parameters of the corresponding noxious and sub-noxious stimuli in a data library; and
- assign one of the quantitative values to a second patient based on a measurement of the level of cortical activity in one or more regions of the second patient's brain, the one quantitative value assigned to the second patient corresponding to a measurement in the data library that is closest to the measurement of the level of cortical activity in the one or more regions of the second patient's brain.

* * * * *